US 7,625,716 B2

(12) United States Patent
Hann

(10) Patent No.: US 7,625,716 B2
(45) Date of Patent: Dec. 1, 2009

(54) METHODS FOR ASSESSING P19-ARF INTERACTIONS IN CMYC

(75) Inventor: Stephen R. Hann, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 892 days.

(21) Appl. No.: 10/997,763

(22) Filed: Nov. 24, 2004

(65) Prior Publication Data
US 2006/0183130 A1    Aug. 17, 2006

Related U.S. Application Data

(60) Provisional application No. 60/525,191, filed on Nov. 26, 2003.

(51) Int. Cl.
G01N 33/574    (2006.01)
(52) U.S. Cl. ........................................ 435/7.23; 514/12
(58) Field of Classification Search .................. None
See application file for complete search history.

(56) References Cited

U.S. PATENT DOCUMENTS

| 5,580,721 A | 12/1996 | Brent et al. |
| 6,586,203 B1 * | 7/2003 | Sherr et al. ............... 435/69.1 |
| 2002/0045192 A1 | 4/2002 | Kriwacki et al. |

FOREIGN PATENT DOCUMENTS

| WO | WO 00/08153 | 2/2000 |
| WO | WO 02/20770 | 3/2002 |
| WO | WO 02/65116 | 8/2002 |

OTHER PUBLICATIONS

Matsumura et al. Cell Cycle 2:4, Jul./Aug. 2003, p. 333-338.*
Eischen et al. Genes and Development 13, p. 2658-2669, 1999.*
Cleveland et al., "Antagonism of Myc functions by Afr", *Cancer Cell,* 6:309-311, 2004.
Qi et al., "p19ARF directly and differentially controls the functions of c-Myc independently of p53", *Nature,* 431:712-717, 2004.
Amanullay et al., "p53-independent apoptosis associated with c-Myc-mediated block in myeloid cell differentiation," *Oncogene,* 19:2967-2977, 2000.
Bates et al., "p14$^{ARF}$ liks the tumour suppressors RB and p53," *Nature,* 395:124-125, 1998.
Berg et al., "Small-molecule antagonists of Myc/Max dimerization inhibit Myc-induced transformation of chicken embryo fibroblasts," *Proc. Natl. Acad. Sci., USA,* 99:3830-3835, 2002.
Bergsmedh et al., "Loss of the p21(Cip1/Waf1) cyclin kinase inhibitor results in propagation of horizontally transferred DNA," *Cancer Res.,* 62(2):575-579, 2002.
Carlson et al., "Tbx3 impinges on the p53 pathway to suppress apoptosis, facilitate cell transformation and block myogenic differentiation," *Oncogene,* 21(24):3827-3835, 2002.

Conzen et al., "Induction of cell cycle progression and acceleration of apoptosis are two separable functions of c-Myc: transrepression correlates with acceleration of apoptosis," *Mol Cell Biol,* 20(16):6008-6018, 2000.
Datta et al., "Myc-ARF (alternate reading frame) interaction inhibits the functions of Myc," *J. Biol. Chem.,* 279:36698-36707, 2004.
Eischen et al., "Disruption of the ARF-Mdm2-p53 tumor suppressor pathway in Myc-induced lymphomagenesis," *Genes Dev,* 13:2658-2669,1999.
Fukasawa et al., "Genomic instability and apoptosis are frequent in p53 deficient young mice," *Oncogene,* 15:1295-1302, 1997.
Haviernik et al., "Consistent inactivation of p19(Arf) but not p15(Ink4b) in murin myeloid cells transformed in vivo by deregulated c-Myc," *Oncogene,* 22(11):1600-1610, 2003.
Honda and Yasuda, "Association of p19(ARF) with Mdm2 inhibits ubiquitin ligase activity of Mdm2 for tumor suppressor p53," *EMBO J,* 18(1):22-27, 1999.
Inoue et al., "Dmp1 is haplo-insufficient for tumor suppression and modifies the frequencies of Arf and p53 mutations in Myc-induced lymphomas," *Genes Dev,* 15(22):2934-2939, 2001.
Jacobs et al., "Bmi-1 collaborates with c-Myc in tumorigenesis by inhibiting c-Myc-induced apoptosis via INK4a/ARF," *Genes Dev,* 13(20):2678-2690, 1999.
Jacobs et al., "The oncogene and polycomb-group bmi-1 regulates cell proliferation and senescence through the ink4a locus," *Nature,* 397(6715):164-168, 1999.
Kamijo et al., "Tumor spectrum in ARF-deficient mice," *Cancer Res.,* 59:2217-2222, 1999.
Korgaonkar et al., "ARF function does not require p53 stabilization or Mdm2 relocalization," *Mol. Cell Biol.,* 2(1):196-206, 2002.
Lenahan and Ozer, "Induction of c-myc mediated apoptosis in SV40-transformed rat fibroblasts," *Oncogene,* 12(9):1847-1854, 1996.
Lindstrom and Wiman, "Myc and E2F1 induce p53 through p14ARF-independent mechanisms in human fibroblasts," *Oncogene,* 22(32):4993-5005, 2003.
Lohrum et al., "Contribution of two independent MDM2-binding domains in p14(ARF) to p53 stabilization," *Curr Biol,* 10(9):539-542, 2000.
Midgley et al., "An N-terminal p14ARF peptide blocks Mdm2-dependent ubiquitination in vitro and can activate p53 in vivo," *Oncogene,* 19(19):2312-2323, 2000.
Ng, "Death associated protein kinase: from regulation of apoptosis to tumor suppressive functions and B cell malignancies," *Apoptosis,* 7(3):261-270, 2002.

(Continued)

*Primary Examiner*—Larry R. Helms
*Assistant Examiner*—Meera Natarajan
(74) *Attorney, Agent, or Firm*—Fulbright & Jaworski

(57) ABSTRACT

The c-Myc oncogene is bound by p19Arf, which inhibits c-Myc's ability to transform cells while augmenting apoptosis. This provides the basis for screening assays that examine the ability of various candidate substances to promote p19Arf interactions, or to substitute therefor.

15 Claims, 8 Drawing Sheets

OTHER PUBLICATIONS

Oster et al., "Functional analysis of the N-terminal domain of the Myc oncoprotein," *Oncogene*, 22:1998-2010, 2003.

Peeper et al., "A functional screen identifies hDRIL1 as an oncogene that rescues RAS-induced senescence," *Nat Cell Biol*, 4(2):148-153, 2002.

Pendergast, "Mechanisms of apoptosis by c-Myc," *Oncogene*, 19(19):2967-2987, 1999.

Pomerantz et al., "The Ink4a tumor suppressor gene product, p19Arf, interacts with MDM2 and neutralizes MDM2's inhibition of p53," *Cell*, 92:713-723, 1998.

Qi et al., "CTCF functions as a critical regulator of cell-cycle arrest and death after ligation of the B cell receptor on immature B cells," *Proc. Natl. Acad. Sci.*, USA, 100(2):633-638, 2003.

Rasko et al., "Cell growth inhibition by the multifunctional multivalent zinc-finger factor CTCF," *Cancer Res.*, 61(16):6002-6007, 2001.

Raveh et al., "DAP kinase activates a p19ARF/p53-mediated apoptotic checkpoint to suppress oncogenic transformation," *Nat Cell Biol*, 3(1):1-7, 2001.

Soucek et al., "Omomyc, a potential Myc dominant negative, enhances Myc-induced apoptosis," *Cancer Res.*, 62:3507-3510, 2002.

Trudel et al., "C-MYC-induced apoptosis in polycystic kidney disease is Bcl-2 and p53 independent," *J Exp Med*, 186:1873-1884, 1997.

Tsuji et al., "p53-independent apoptosis is induced by the $p19^{ARF}$ tumor suppressor," *Biochim Biophys Res Commun*, 295:621-629, 2002.

Weber et al., "Nucleolar Arf sequesters Mdm2 and activates p53," *Nat Cell Biol*, 1(1):20-26, 1999.

Weber et al., "p53-independent functions of the $p19^{ARF}$ tumor suppressor," *Genes Dev.*, 14(18):2358-2365, 2000.

Wood et al., "Early gene expression changes preceding thyroid hormone-induced involution of a thyrotrope tumor," *Endocrinology*, 143(2):347-359, 2002.

Xiao et al., "Transactivation-defective c-MycS retains the ability to regulate proliferation and apoptosis," *Genes Dev.*, 12:3803-3808, 1998.

Zhang et al., "ARF promotes MDM2 degradation and stabilizes p53: ARF-INK4a locus deletion impairs both the Rb and p53 tumor suppression pathways," *Cell*, 92:725-734, 1998.

Zindy et al., "Myc signaling via the ARF tumor suppressor regulates p53-dependent apoptosis and immortalization," *Genes Dev.*, 12:2424-2433, 1998.

* cited by examiner

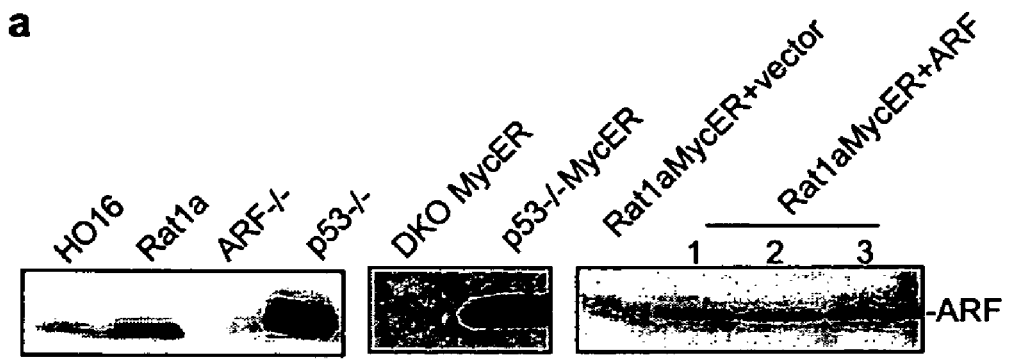
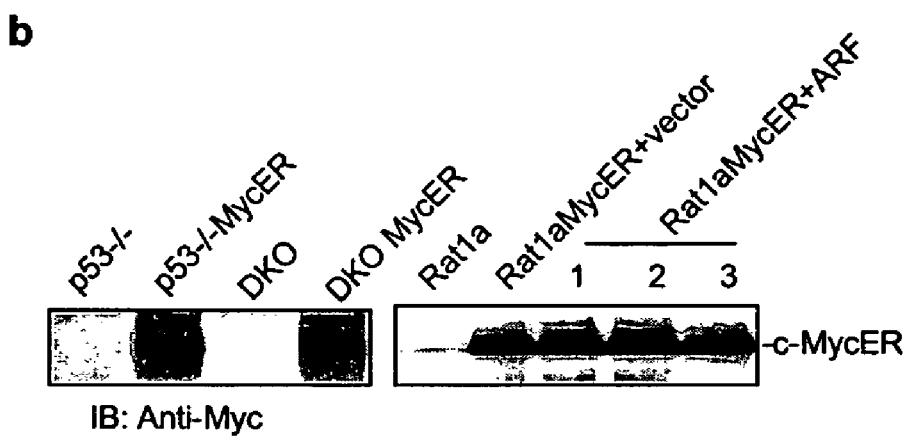
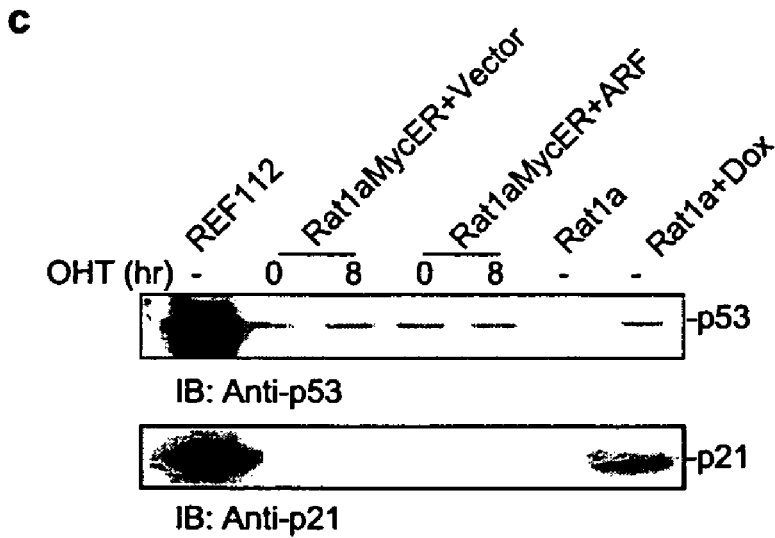
FIG. 7A–C

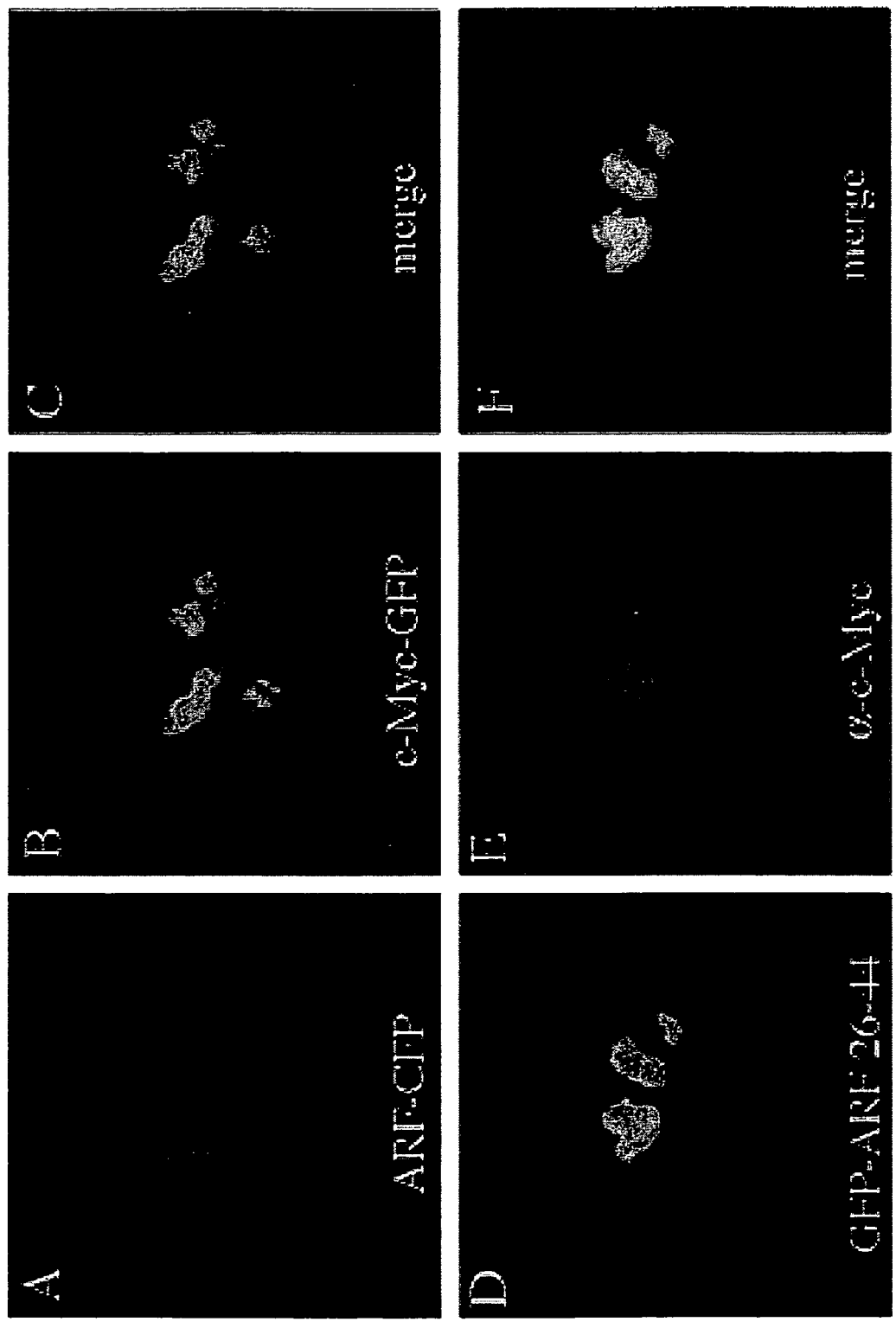
FIG. 8A-F

US 7,625,716 B2

METHODS FOR ASSESSING P19-ARF INTERACTIONS IN CMYC

The present application claims benefit of priority to U.S. Provisional Application Ser. No. 60/525,191, filed Nov. 26, 2003, the entire contents of which are hereby incorporated by reference.

This invention was made with government support under grant number RO1 CA47399 awarded by the National Cancer Institute. The government has certain rights in the invention.

BACKGROUND OF THE INVENTION

1. Field of the Invention

The present invention relates to the fields of molecular biology and oncology. More specifically, it deals with the identification of a molecular interaction between the product of the c-myc oncogene and p19Arf. The present invention also provides for methods of identifying agents that alter this interaction.

2. Description of Related Art

Numerous studies have demonstrated an essential role for the c-myc gene in the control of cell proliferation. Deregulated c-myc expression has been demonstrated in many types of human cancer, including Burkitt's lymphoma, myeloid and plasma cell leukemia, breast carcinoma, cervical carcinoma, small cell lung carcinoma, colon carcinoma, osteosarcoma, and glioblastoma (Oster et al., 2002; Spencer and Groudine, 1991). Overexpression studies illustrate the diverse biological activities of c-myc, including the ability to stimulate cellular proliferation, cause cellular immortalization, inhibit terminal differentiation (Henriksson and Luscher, 1996; Lemaitre et al., 1996), induce apoptosis in cells deprived of survival factors (Askew et al., 1991; Bissonnette et al., 1994), contribute to genomic instability and chromosomal alterations (Felsher and Bishop, 1999; Li and Dang, 1999), transform cells in vitro, and cause tumorigenesis (Facchini and Penn, 1998; Henriksson and Luscher, 1996).

The c-Myc protein is a transcription factor that has been shown to both upregulate and downregulate a variety of target genes. Heterodimerization with its protein partner, Max, is required for sequence-specific DNA binding to a specific E box element as well as for biological activity (Oster et al., 2002). Transactivation of target gene promoters by c-Myc also requires binding of factors to the amino-terminal trans-activation domain, such as TRRAP and Tip48/49 (Oster et al., 2002). c-Myc upregulates several proliferative genes, such as cyclin D, cyclin E, and cdk4 (Oster et al., 2002). Also, anti-proliferative genes, such as cyclin-dependent kinase inhibitors (CDK-I) $p21^{Cip1}$, $p15^{Ink4b}$, $p27^{Kip1}$, and several of the gadd genes, can be repressed by c-Myc to facilitate cell cycle progression (Oster et al., 2002). The tumor suppressor, $p19^{ARF}$ (ARF), which is induced by c-Myc, Ras and E2F, mediates p53 activation by sequestering Mdm2 and thus inhibiting the Mdm2-dependent degradation of p53 (Bates et al., 1998; Pomerantz et al., 1998; Zhang et al., 1998; Zindy et al., 1998). Inactivation of the ARF-Mdm2-p53 pathway allows oncogenic c-Myc to drive cell cycle progression without apoptosis (Eischen et al., 1999). Unchecked cell cycle progression leads to transformation and tumorigenesis, as illustrated by the observation that mice lacking ARF are highly prone to tumor development (Haviernik et al., 2003; Kamijo et al., 1999).

SUMMARY OF THE INVENTION

Thus, in accordance with the present invention, there is provided a method of screening a candidate substance comprising (a) providing an isolated c-Myc polypeptide; (b) mixing the c-Myc polypeptide with a candidate substance; (c) mixing the mixture of step (b) with p19Arf polypeptide; and (d) measuring the interaction of p19Arf and c-Myc polypeptides, wherein a decrease in p19Arf polypeptide binding to c-Myc polypeptide, as compared to the binding of p19Arf polypeptide to c-Myc polypeptide in the absence of the candidate substance, identifies the candidate substance as a p19Arf mimic. The p19Arf and c-Myc polypeptides may be murine polypeptides, for example, having the sequence of SEQ ID NO:1, respectively. At least one of the p19Arf and c-Myc polypeptides may be labeled, or both may be labeled, thereby permitting measurement of fluorescence resonance energy transfer. The candidate substance may be a peptide, a polypeptide, a oligonucleotide, a polynucleotide, or small molecule. Step (c) may comprise separation by gel electrophoresis or immunologic detection. The method may further comprise a washing step between steps (b) and (c). c-Myc polypeptide may be bound to a support, such as a column, a bead, a dipstick, a microtiter well or a test tube. In support-based assays, step (d) may comprise measuring p19Arf bound to the support, and further, p19Arf polypeptide may be labeled, and step (d) may comprise measuring label associated with the support. Alternatively, step (d) may comprise contacting the support with an anti-p19Arf antibody that binds p19Arf polypeptide when bound to c-Myc polypeptide.

In another embodiment, there is provided a method of screening a candidate substance comprising (a) providing an isolated p19Arf polypeptide and an isolated c-Myc polypeptide; (b) mixing the p19Arf and c-Myc polypeptides with a candidate substance; and (c) measuring the interaction of p19Arf and c-Myc polypeptides in the mixture of step (b), wherein a decrease in p19Arf polypeptide binding to c-Myc polypeptide, as compared to the binding of p19Arf polypeptide to c-Myc polypeptide in the absence of the candidate substance, identifies the candidate substance as a p19Arf mimic. The p19Arf and c-Myc polypeptides may be murine polypeptides, for example, having the sequence of SEQ ID NO:1, respectively. At least one of the p19Arf and c-Myc polypeptides may be labeled, or both may be labeled, thereby permitting measurement of fluorescence resonance energy transfer. The candidate substance may be a peptide, a polypeptide, a oligonucleotide, a polynucleotide, or small molecule. Step (c) may comprise separation by gel electrophoresis or immunologic detection. The method may further comprise a washing step between steps (b) and (c).

In still yet another embodiment, there is provided a method of screening a peptide for c-Myc binding activity comprising (a) providing a peptide; (b) contacting the peptide with a c-Myc polypeptide; (c) measuring peptide bound to the c-Myc polypeptide, wherein detection of c-Myc polypeptide-bound peptide identifies the peptide as having c-Myc polypeptide-binding activity. The peptide may be a p19Arf polypeptide, for example, as produced by proteolytic degradation of p19Arf polypeptide. The peptide may be produced by chemical synthesis. The peptide is a member of a randomly generated peptide library, or part of a phage display library. The peptide may be radioactively, fluorescently or chemilluminescently labeled. The peptide and the c-Myc polypeptide may be labeled, and step (c) may comprise measuring fluorescence resonance energy transfer.

In a further embodiment, there is provided a method of screening for c-Myc inhibitors comprising (a) providing a cell expressing c-Myc and containing an expression construct comprising a c-Myc responsive promoter fused to a nucleic acid segment encoding a detectable marker; (b) contacting the cell with a p19Arf peptide or mimetic; (c) measuring marker activity, wherein a decrease in marker activity, as compared to a cell not contacted with the p19Arf peptide or mimetic, identifies the p19Arf peptide or mimetic as a c-Myc inhibitor. The marker may be luciferase, green fluorescent protein, red fluorescent protein, or cyan fluorescent protein.

In yet an additional embodiment, there is provided a method of treating a patient having a c-Myc related cancer comprising (a) identifying a cancer as c-Myc-related; and (b) contacting a cell of the cancer with a p19Arf polypeptide, a p19Arf peptide or a p19Arf mimetic. The contacting may comprise administering to the patient a p19Arf polypeptide, a p19Arf peptide or a p19Arf mimetic, or administering to the patient a p19Arf expression construct. The expression construct may be a viral or non-viral expression construct. The method may further comprise contacting the cancer cell with a second anti-cancer therapy.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C, $p53^{-/-}$ MEFs immunostained for ARF and nucleolin. FIGS. 1D-F, $p53^{-/-}$ MEFs transfected with c-Myc-YFP and immunostained for ARF. FIGS. 1G-I, $p53^{-/-}$ MEFs transfected with c-Myc and immunostained for c-Myc and ARF. FIGS. 1J-L, Wild-type MEFs transfected with c-Myc and immunostained for c-Myc and ARF. Cells were visualized by fluorescence microscopy.

FIGS. 2A-D, Coimmunoprecipitation of ARF and c-Myc. Cos-7 cells transfected with c-Myc and/or ARF were subjected to immunoprecipitation (IP) using anti-Mycfl (fl, full length; FIG. 2A) or anti-ARF (FIG. 2B) followed by immunoblot (IB) analysis using the indicated antibody. FIG. 2C, $\text{c-myc}^{-/-}$ cells, $\text{ARF}^{-/-}$ MEFs or $p53^{-/-}$ MEFs were subjected to IP using anti-Mycfl followed by IB analysis. FIG. 2D, HeLa cells were subjected to IP using anti-p14ARF or anti-Mycfl followed by IB analysis. FIG. 2E, Coimmunoprecipitation of c-Myc deletions with ARF. Cos-7 cells transfected with the indicated c-Myc deletion mutant were subjected to IP with anti-ARF followed by IB analysis. FIG. 2F, Schematic representation of the structure of c-Myc and c-Myc deletions showing relative binding to ARF.

FIG. 3D, Quantitative realtime PCR analysis of c-Myc target gene expression in $p53^{-/-}$ MycER MEFs and DKO MycER MEFs with or without c-MycER activation (±OHT). ARF and c-MycER expression in these cell lines was confirmed by IB analysis (FIGS. 7A and 7B). FIG. 3E, Recruitment of ARF to c-Myc target gene promoters. Chromatin prepared from $p53^{-/-}$ MycER and DKO MycER cells (±OHT) was subjected to IP using anti-ARF followed by PCR using primers for the eIF4E and nucleolin promoters.

FIG. 4A, Proliferation assay of $p53^{-/-}$ MycER and DKO MycER MEFs with or without c-MycER activation (±OHT). FIG. 4B, $p53^{-/-}$ MycER or DKO MycER MEFs (±OHT) were assayed for apoptotic cell death. FIG. 6C, Proliferation assay of Rat1a MycER±ARF cell lines without MycER activation. ARF and c-MycER expression in these cell lines was confirmed by IB analysis (FIGS. 7A and 7B). FIG. 4D, Proliferation assay of Rat1a cell lines with MycER activation. FIG. 4E, Rat1a cell lines (±OHT) were assayed for apoptosis in low serum. FIG. 4F, Rat1a cell lines (±OHT) were plated in soft agar and analysed for colony growth.

FIG. 5A, The reporter construct cul1-luc (left panel) or pdgf br-luc (right panel) were transfected into ARF-/- MEFs, p53-/-MEFs with either empty vector or c-Myc with or without ARF. Reporter activity was determined as described in Methods. The expression of c-Myc and ARF proteins was determined by immunoblotting with anti-Mycfl and anti-ARF (lower panels). FIG. 5B, Quantitative Real-Time PCR analysis of c-Myc target genes in p53-/- MycER and DKO MycER MEFs. RNA was isolated from p53-/- MycER and DKO MycER MEFs treated with 1 mM OHT for the indicated times and analyzed as described in Methods. FIG. 5C, Northern blot analysis of cad, eIF4E and gadd45 in Rat1a cells expressing c-MycER with or without ARF. RNA was isolated from Rat1a MycER or Rat1a MycER+ARF cells treated with 5 mM OHT for the indicated times and analyzed by Northern blot analysis. The data was converted into -fold induction and plotted over time.

FIGS. 7A-C—Analysis of protein expression in various cell lines. FIG. 7A, IB analysis of ARF in different monoclonal cell lines. Cell lysates were prepared from c-myc-/- (HO16), Rat1a, p53-/- MEF, ARF-/- MEF, p53-/- MycER MEF, DKO MycER MEF, Rat1a MycER and Rat1a MycER+ARF cells and IB analysis was performed using anti-ARF for endogenous ARF expression (left and middle panel), or for exogenous ARF expression (right panel). FIG. 7B, IB analysis of c-MycER in different monoclonal cell lines. p53-/- MEF, p53-/- MycER MEF, DKO, DKO MycER MEF, Rat1a MycER and Rat1a MycER+ARF cells were lysed and subjected to IB analysis with anti-Mycfl. FIG. 7C, IB analysis of endogenous p53 and p21 in Rat1a MycER cell lines following c-Myc activation. Cell lysates were prepared from Rat1a MycER, Rat1a MycER+ARF cells treated with 5 mM OHT for the indicated times, REF112 cells that overexpress wild-type p53, and Rat1a cells treated with or without 0.5 mM doxorubicin for 16 hr, and IB analysis was performed using anti-p53 (pAb240; Santa Cruz, upper panel) or anti-p21 (M-19; Santa Cruz, lower panel).

FIGS. 8A-F—Amino acids 26-44 of ARF are sufficient to target c-Myc to nucleoli. Cos-7 cells were cotransfected with ARF-CFP and c-Myc-GFP (FIGS. 8A-C) or wih GFP-ARF 26-44 and untagged c-Myc (FIGS. 8D-F). Forty-eight hours after transfection, cells were fixed using paraformaldehyde and, for FIGS. 8D-F, cells were immunostained using anti-c-

Figure 1:
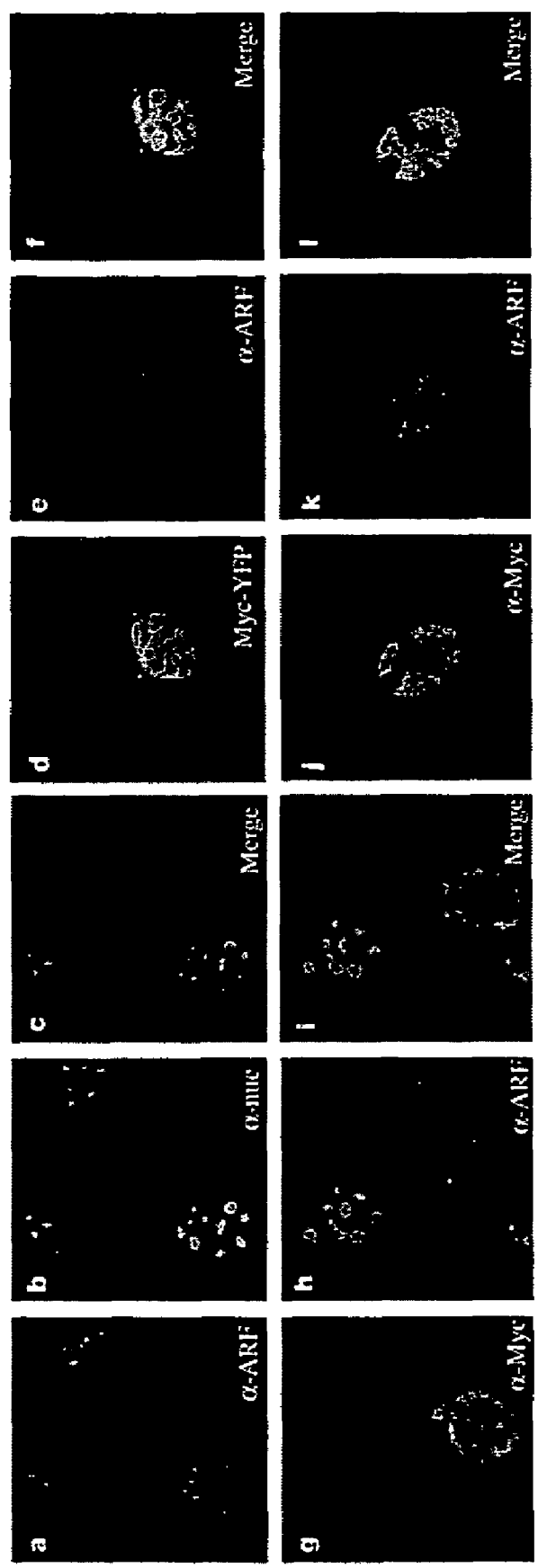
FIGS. 1A-L—Endogenous ARF colocalizes with c-Myc in the nucleoplasm upon c-Myc overexpression.

Myc. Cells were visualized with fluorescence microscopy using a 63× objective with the appropriate filters.

DESCRIPTION OF ILLUSTRATIVE EMBODIMENTS

I. The Present Invention

The inhibition of c-Myc-induced transactivation and transformation by p19Arf is highly specific, since p19Arf does not inhibit c-Myc repression of genes, normal cell proliferation or apoptosis induced by c-Myc. Since many tumors lose the p19Arf gene and have deregulated c-Myc, the inventors propose that p19Arf mimics are therapeutic agents for the inhibition of c-Myc-induced transformation/tumorigenesis, while not inhibiting normal cell proliferation and apoptosis. It has also been shown that deactivation of an inducible c-Myc results in the sustained regression of tumors (Felsher and Bishop, 1999; Jain et al., 2002)), suggesting that c-Myc is an excellent target for the inhibition of tumorigenesis. Specific chemical compoundss can antagonize Myc/Max dimerization and inhibit transformation (Berg et al., 2002). However, inhibition of the c-Myc/Max heterodimerization is not as specific as p19Arf inhibition, since Max is critical for all functions of c-Myc, and inhibition of its functions would likely inhibit normal cell proliferation and apoptosis. Thus, the present invention provides for a variety of assays to screen for p19Arf mimics, and for the provision of p19Arf-based therapies.

II. c-Myc c-Myc is a transcription factor that has been associated with a number of different cancers. It is a 439 amino acid, 64 kDa protein, with O-linked glycosylation and phosphorylation sites. It is characterized by N-terminal domains, termed Myc boxes, which are found in the closely related protein N-Myc and L-Myc. The C-terminal region contains a dimerization motif, termed helix-loop-helix leucine zipper, which permits homotypic or heterotypic dimerization. Max dimerization with c-Myc generates a DNA-binding complex that activates transcription through the amino-terminal 143 amino acids. A small segment of this region is also required for c-Myc-mediated transcription repression. The N-terminal domain of c-Myc also is required for transformation.

c-Myc is known to interact with a host of other cellular proteins, including MM-1, v-raf, c-Raf, SMAD2, MEK1, RelA, α-tubulin, TRRAP, Smad3, p73, Tata box binding protein, Transcription factor IIF (α-subunit), p107, Nuclear transcription factor Y γ-subunit, Max-like protein X, CBF-C/NF-YB, BRAC1, YY1, Zinc finger protein 151, N-Myc interactor, Pam, Transcription factor AP-2β, Retinoblastoma 1, JNK1, SMARCB1, p34cdc2, AMY-1, HSP 90A, Tubulin α-2, Tubulin α (ubiquitous), Zinc finger protein 151, Tubulin α-8, ERK5, Tubulin α (brain specific), Nuclear transcription factor Y β-subunit, Tubulin α-1, and Max interacting protein 1.

Expression of c-Myc is tightly regulated by external signals. The resting cell expresses little c-Myc, whereas cells stimulated by growth factors dramatically increase c-Myc expression. Abnormal expression of c-Myc invokes p19Arf- and p53-dependent pathways, which should eliminate such cells by induction of apoptosis. c-Myc is required for normal embryonic development. However, activation of the c-myc gene in adult cells can lead to development of cancers. Chromosomal translocations, as in the case of Burkitt's lymphoma, activate transcription of the c-myc gene by relocating it in the proximity of highly transcribed immunoglobulin genes. c-myc gene amplification (50-200 copies) also is found in cancer cells. Other mechanisms of c-Myc overexpression include increased transcriptoion, removal of 3'-UTR destabilizing sequences, retroviral insertion, and post-translational modification.

III. p19ARF

The p19 alternative reading frame (p19Arf) protein leads to growth arrest or apoptosis of cells exposed to inappropriate mitogenic stimuli. p19Arf-expressing cells undergo p53 pathway activation, followed by cell cycle arrest or apoptosis, depending on the cell context. In multiple settings, the biological effects of p19Arf, such as growth arrest or suppression of transformation, appeared to depend largely on the maintenance of intact p53 signal transduction. ARF also limits the ability of Mdm2 to ubiquitinate p53 in vitro (Honda and Yasuda 1999; Midgley et al., 2000) and in vivo. Binding of ARF to Mdm2 involves two separate domains of both the mouse p19$^{ARF}$ and human p14$^{ARF}$ proteins that interact cooperatively with a central acidic segment of Mdm2 (Lohrum et al., 2000; Weber et al., 2000). Although ARF localizes to the nucleolus on its own, ARF binding unmasks a cryptic nucleolar localization signal within the carboxy-terminal Mdm2 RING domain, the integrity of which is required for localization of the binary complex to the nucleolus (Lohrum et al., 2000b; Weber et al., 2000). Disruption of the Mdm2 nucleolar localization signal enables Mdm2 to retain ARF in the nucleoplasm.

Recent reports demonstrate that p19Arf can also inhibit cell growth in the absence of p53. In one case, growth inhibition depended on the simultaneous presence of p16INK4A and MDM2 proteins. In another, it depended on the absence of MDM2. ARF has been shown to bind directly to Mdm2, sequestering it in the nucleolus and enabling transcriptionally active p53 to accumulate in the nucleoplasm (Weber et al., 1999). The mechanism underlying p19Arf-dependent growth inhibition of p53-null cells remains obscure, although ectopic overexpression of E2F1 overcame this effect in certain cell species. These findings have led to speculation that, in addition to p53, p19Arf targets E2F1 and/or other E2F family members leading to a decrease in function.

Murine p19Arf is shown in SEQ ID NO:1. Human p14Arf, which may be substituted for any mention of p19Arf herein, is shown in SEQ ID NO:29.

IV. Screening Methods

The present invention comprises various methods for identifying compounds that can modulate or substitute for the p19Arf interaction with c-Myc. These assays may comprise random screening of large libraries of candidate substances; alternatively, the assays may be used to focus on particular classes of compounds selected with an eye towards structural attributes that are believed to make them more likely to mimic p19Arf.

To identify a useful candidate substance, one generally will determine the ability of the substance to compete for binding of p19Arf with c-Myc. For example, a method generally comprises:

(a) providing a candidate substance;
(b) mixing the candidate substance with an c-Myc molecule;
(c) mixing the substance/c-Myc with p19Arf; and
(d) measuring the binding of p19Arf with c-Myc, where a difference between the binding observed in step (d), as compared to the binding observed in the absence of the candidate substances, indicates that the substance binds c-Myc. Such assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially act as a p19Arf mimic, or otherwise regulate the activity of c-Myc in a p19Arf-like fashion. The candidate substance may be a protein or fragment thereof, a small molecule, or even a nucleic acid molecule. It may prove to be the case that the most useful pharmacological compounds will be compounds that are structurally related to p19Arf itself. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

In addition to the compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Of particular interest here are competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate c-Myc activity in cells. Various cell lines can be utilized for such screening assays, including cells specifically engineered for this purpose. Cells may be generated that express appropriate amounts of c-Myc and p19Arf under regulatable promoters. For example, cells that constitutively express c-Myc, and hence are immortalized. These cells would also comprise an expression construct for p19Arf, where the construct expresses p19Arf only upon induction. Thus, once induced, cells with cease to proliferate and undergo apoptosis unless an appropriate competitor (and hence potential mimic) of p19Arf is employed. Depending on the assay, culture may be required.

Cells may be examined using any of a number of different physiologic assays. One may employ terminal deoxynucleotidyl transferase mediated dUTP-biotin nick end labeling (TUNEL) assays to measure the integrity of DNA (Gorczyca, 1993). This assay measures the fragmentation of DNA by monitoring the incorporation of labeled UTP into broken DNA strands by the enzyme terminal transferase. The incorporation can be monitored by electroscopy or by cell sorting methodologies (e.g., FACS). Alternatively, molecular analysis may be performed, for example, looking at protein expression, mRNA expression (including differential display of whole cell or polyA RNA) and others.

Other characteristics of apoptosis include Annexin-V staining, caspase activation, and DNA fragmentation. For example, one may look at DNA fragmentation using a separative method, e.g., chromatography or electrophoresis, to size fractionate the sample. An exemplary assay involves the isolation of DNA from cells, followed by agarose gel electrophoresis and staining with ethidium bromide. DNA fragmentation, characteristic of apoptosis, will be visualized as "ladders" containing a wide range of fragment sizes.

One also may examine cells using standard light or electron microscopy to assess the presence or absence of the cytopathologies characteristic of apoptosis. Those of skill in the art, applying standard methods of microscopy, will be able to assess cytopathology. In a variation, one may use microscopy in combination with staining procedures, such as Annexin V-7AAD or PI staining. Also contemplated is sub G0/1 cell analysis.

Finally, though an indirect assessment of apoptosis, one may employ caspase activity assays. Commercial kits are available, for example, from Chemicon International (CleavaLite™ Bioluminescent Caspase-3 Activity Assay Kit) and Roche Diagnostics (Caspase 3 Activity Assay).

D. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies the substance as a useful compound. In the context of the present invention, in vivo screens are likely to be considered as secondary screens for compounds identified using cell free, in vitro and in cyto studies.

Treatment of animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

E. Co-Immunoprecipitation

Protein-protein interactions may also be studied by using biochemical techniques such as cross-linking, co-immunoprecipitation, and co-fractionation by chromatography, which are well known to those skilled in the art. The co-immunoprecipitation technique consists of (i) generating a cell lysate; (ii) adding an antibody to the cell lysate; (iii) precipitating and washing the antigen; and (iv) eluting and analyzing the bound proteins (Phizicky and Fields, 1995). The antigen used to generate the antibody can be a purified protein, or a synthetic peptide coupled to a carrier. Both monoclonal and polyclonal antibodies can be utilized in co-immunoprecipitation, or alternatively, a protein can be used which carries an epitope tag recognized by a commercially available antibody.

F. Fluorescence Energy Transfer (FRET)

Two GFP variants, cyan fluorescent protein (CFP) and yellow fluorescent protein (YFP), have special fluorescence excitation and emission properties that are well suited to measurement of close molecular distances. When these two molecules are positioned at distances within 7 nm of each other, energy transfer can occur from the excited state of the donor molecule (CFP), to the unoccupied excited state of the acceptor molecule (YFP) by a process commonly referred to as fluorescence resonance energy transfer (FRET). FRET between CFP and YFP can be detected using a wide variety of spectroscopic and fluorescence microscopy techniques and is often used to report protein-protein interactions or changes in the conformation state of a peptide or protein. Since the efficiency of FRET is directly related to the spectroscopic properties of both the donor and acceptor molecules, improvements can be made to the fluorescence properties of the fluorophores, such as to increase both the FRET efficiency and the chances of successful detection. FRET has also been used to quantify association of a protein of interest with an organelle (Chiu et al. 2002).

The overall FRET efficiency is determined by several factors and is directly related to the amount of overlap between the absorption spectra of the acceptor molecule and the emission spectra of the donor molecule. The FRET efficiency is also affected by the ability of the donor molecule to absorb light, as indicated by its molar extinction coefficient, and the overall stability of the excited state, as indicated by the probability that absorption will lead to fluorescence (quantum yield) and the lifetime of the excited state. Although CFP is the most commonly used donor for FRET using fluorescent proteins, there are a number of disadvantages for its use in the FRET reaction. The molar extinction coefficient and the quantum yield of CFP are much less than the other commonly used fluorescent proteins. As a result CFP is typically 5-fold less bright than the acceptor molecule. Furthermore, CFP has two fluorescent states of unequal brightness. This results in a two-component excited-state fluorescence lifetime, which is disadvantageous for detection of FRET using fluorescence lifetime measurements. In addition, this leads to quenching of CFP fluorescence when it is in close proximity to another CFP molecule by a process known as homotransfer.

The present invention describes changes made to the spectroscopic properties of CFP that are specifically designed to improve the properties of CFP as a donor for FRET. Specifically, mutations were introduced into CFP in order to improve its molar extinction coefficient and quantum yield, and produce a single component excited state lifetime. The oCFP of the present invention is thus used as a donor fluorescent protein (DFP) for FRET studies. An acceptor fluorescent protein (AFP) may be green fluorescent protein, red fluorescent protein, yellow fluorescent protein, EGFP, EYFP, Venus, Citrine, phiYellow, copGreen CGFP, ECFP, oCFPs, fluoroscein, rhodamine, Oregon Green, or Alexa-488. In fact, practically any chromophore capable of resonance energy transfer with CFP, i.e., with absorbance between 450 and 600 nm, may be used, including dyes, fluorophores and non-fluorescent proteins that are capable of energy absorbance in the appropriate range (Forster, 1948; Patterson et al., 2000).

The types of the microscope can be suitably selected depending on the purpose. If frequent observations are necessary for monitoring a time course of the changing, conventional incident-light fluorescent microscope is preferred. If resolution is to be increased as in the case where detailed intercellular localization is to be monitored, confocal laser microscope is preferred. As a microscope system, an inverted microscope is preferred in view of keeping the physiological state of cell and preventing contamination. When erecting microscope is used, an immersion lens can be used in the case of using lens of high power.

The filter set can be suitably selected depending on the fluorescent wave length of the fluorescent protein. For the observation of GFP, it is preferred to use a filter with excitation light of about 470-490 nm and fluorescent light of about 500-520 nm. For the observation of YFP, it is preferred to use a filter with excitation light of about 480-500 nm and fluorescent light of about 510-550 nm. For the observation of CFP, it is preferred to use a filter with excitation light of about 425-445 nm and fluorescent light of about 460-500 nm.

Moreover, when time course observation is carried out in living cells by using a fluorescent microscope, the cells should be photographed in a short period, and therefore a high sensitive cooled CCD camera is used. By using a cooled CCD camera, thermal noise can be decreased by cooling CCD, and weak fluorescent image can be clearly photographed by exposure of short period.

V. Recombinant Technologies

DNA vectors form encoding p19Arf or fragments thereof are important further aspects of the present invention. The term "expression vector or construct" means any type of genetic construct containing a nucleic acid coding for a gene product in which part or all of the nucleic acid encoding sequence is capable of being transcribed into mRNA, and optionally translated into a protein. Thus, in certain embodiments, the present invention contemplates vectors for the delivery and expression of p19Arf.

Expression is facilitated by placing the coding portion of a DNA segment, whether encoding a full length protein or smaller peptide, under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

The promoter may be in the form of the promoter that is naturally-associated with a gene, as may be obtained by isolating the 5' non-coding sequences located upstream of the coding segment or exon, for example, using recombinant cloning and/or PCR™ technology, in connection with the compositions disclosed herein. Alternatively, the promoter may be "heterologous" to the coding sequence, i.e., not naturally-associated therewith.

It may be important to employ a promoter that effectively directs the expression of the DNA segment in a particular cell type, organism, or even animal. The use of promoter and cell type combinations for protein expression is generally known to those of skill in the art of molecular biology, for example, see Sambrook et al. (2001), incorporated herein by reference. The promoters employed may be constitutive, or inducible, and can be used under the appropriate conditions to direct high level expression of the introduced DNA segment, such as is advantageous in the large-scale production of recombinant proteins or peptides.

Of particular use are promoters and enhancers that direct transcription of genes that are specific for or highly expressed in cancer cells. In various other embodiments, high level constitutive promoters are desired, such as the human cytomegalovirus (CMV) immediate early gene promoter, the SV40 early promoter and the Rous sarcoma virus long terminal repeat can be used to obtain high-level expression of nucleic acids. The use of other viral or mammalian cellular or bacterial phage promoters which are well-known in the art to achieve expression are contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In order to mediate the effect transgene expression in a cell, it will be necessary to transfer the expression vectors of the present invention into a cell. Such transfer may employ viral or non-viral methods of gene transfer. This section provides a discussion of methods and compositions of gene transfer.

A. Viral Vector-Mediated Transfer

The p19Arf constructs may be incorporated into an infectious particle to mediate gene transfer to a cell. Additional expression constructs as described herein may also be transferred via viral transduction using infectious viral particles, for example, by transformation with an adenovirus vector of the present invention as described herein below. Alternatively, lentiviral, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral vectors, as discussed below.

Adenovirus. Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus. AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Flotte and Carter, 1995; Chatterjee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Lentivirus. Lentivirus vectors based on human immunodeficiency virus (HIV) type 1 (HIV-1) constitute a recent development in the field of gene therapy. A key property of HIV-1-derived vectors is their ability to infect nondividing cells. High-titer HIV-1-derived vectors have been produced. Examples of lentiviral vectors include White et al. (1999), describing a lentivirus vector which is based on HIV, simian immunodeficiency virus (SIV), and vesicular stomatitis virus (VSV) and which the inventors refer to as HIV/SIVpack/G. The potential for pathogenicity with this vector system is minimal. The transduction ability of HIV/SIVpack/G was demonstrated with immortalized human lymphocytes, human primary macrophages, human bone marrow-derived CD34(+) cells, and primary mouse neurons. Gasmi et al. (1999) describe a system to transiently produce HIV-1-based vectors by using expression plasmids encoding gag, pol, and tat of HIV-1 under the control of the cytomegalovirus immediate-early promoter.

Other Viral Vectors. Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

B. Non-Viral Transfer

DNA constructs of the present invention are generally delivered to a cell, in certain situations, the nucleic acid to be transferred is non-infectious, and can be transferred using non-viral methods. Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell, the nucleic acid may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

VI. Protein Purification

It may be desirable to purify proteins in accordance with the present invention. Protein purification techniques are well known to those of skill in the art. These techniques involve, at one level, the crude fractionation of the cellular milieu to polypeptide and non-polypeptide fractions. Such methods may include physical disruption followed by centrifugation, solvent extraction, salting-out (e.g., by ammonium sulfate or the like), desalting, precipitation, etc.

Having thus separated generally the polypeptide from other molecules, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

The term "purified protein" as used herein is intended to refer to a proteinaceous composition, isolated from other components, wherein the protein or peptide is purified to any degree relative to its naturally-obtainable state. A purified protein or peptide therefore also refers to a protein or peptide, free from the environment in which it may naturally occur. Generally, "purified" will refer to a protein composition that has been subjected to fractionation to remove various other components, and which composition substantially retains its expressed biological activity. Where the term "substantially purified" is used, this designation will refer to a composition in which the protein forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

There is no general requirement that the protein always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VII. Cancer Therapies

In addition to aforementioned screening assays, the present invention also provides for the use of p19Arf and p19Arf mimics as therapeutic agents in the treatment of cancers associated with deregulated c-Myc. c-Myc overexpression has been associated with a wide variety of malignant states, including 80% of breast cancers, 70% of colon cancers, 90% of gynecologic cancers and 50% of hepatocellular carcinomas. Thus, it is proposed that introducing p19Arf or p19Arf mimics into these types of tumor cells will result in reduced cellular proliferation, growth arrest, and/or induction of apoptosis.

A. Protein/Peptide Therapy

A therapy approach is the provision, to a subject, of p19Arf polypeptide, of active fragments, synthetic peptides, mimetics or other analogs thereof. The protein may be produced by recombinant expression means or, for smaller peptides, generated by a peptide synthesizer. Formulations would be selected based on the route of administration and purpose, including but not limited to liposomal formulations and classic pharmaceutical preparations.

B. Genetic-Based Therapies

One of the therapeutic embodiments contemplated by the present inventors is the intervention, at the molecular level, in the events involved in the carcinogenesis. Specifically, the present inventors intend to provide, to a cancer cell, an expression construct capable of providing a p19Arf, or a c-Myc-binding fragment thereof, to that cell. The lengthy discussion above of expression vectors and the genetic elements employed therein is incorporated into this section by reference. Particularly preferred expression vectors are viral vectors, discussed elsewhere in this document.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for different disease types. The section below on routes contains an extensive list of possible routes. In a different embodiment, ex vivo gene therapy is contemplated. In an ex vivo embodiment, cells from the patient are removed and maintained outside the body for at least some period of time. During this period, a p19Arf gene is delivered to these cells, after which the cells are reintroduced into the patient.

In some embodiments of the present invention a subject is exposed to a viral vector and the subject is then monitored for expression construct-based toxicity, where such toxicity may include, among other things, causing a condition that is injurious to the subject.

C. Pharmaceutical Formulations and Delivery

In a preferred embodiment of the present invention, a method of treatment for cancer by the delivery of an expression construct encoding a p19Arf polypeptide, peptide or mimic is contemplated. Cancers may include those such as breast cancer, prostate cancer, lung cancer, brain cancer, liver cancer, testicular cancer, colon cancer, pancreatic cancer, thyroid cancer, head & neck cancer, ovarian cancer, uterine cancer, stomach cancer, melanoma, leukemia, lymphoma, esophageal cancer, or bone cancer.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

The therapeutic expression construct expressing a p19Arf polypeptide, peptide or mimic may be administered by any of the routes and the route of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. Treatment regimens may vary as well, and often depend on disease progression, and health and age of the patient. The clinician will be best suited to make such decisions based on the known efficacy and toxicity (if any) of the therapeutic formulations.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermolysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vaccuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The terms "contacted" and "exposed," when applied to a cell, are used herein to describe the process by which a therapeutic construct encoding a HA4 polypeptide is delivered to a target cell.

D. Combination Therapies

In order to increase the therapeutic effectiveness of a p19Arf polypeptide, peptide, mimic or gene therapy, it may be desirable to combine such compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Moreover, tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that a p19Arf polypeptide, peptide, mimic or gene therapy could be used similarly in conjunction with chemotherapeutic, radiotherapeutic, or immunotherapeutic intervention, in addition to other pro-apoptotic or cell cycle regulating agents.

Alternatively, the a p19Arf polypeptide, peptide, mimic or gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the p19Arf therapy is "A" and the secondary agent, such as radio- or chemotherapy, is "B":

A/B/A B/A/B B/B/A A/A/B A/B/B B/A/A A/B/B/B
B/A/B/B

B/B/B/A B/B/A/B A/A/B/B A/B/A/B A/B/B/A B/B/A/A

B/A/B/B B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with Ad-mda7 gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4. Genes

In yet another embodiment, the secondary treatment is a gene therapy (other than p19Arf) in which a therapeutic polynucleotide is administered before, after, or at the same time a p19Arf therapy is employed. If p19Arf is being delivered via gene therapy, a vector encoding a p19Arf may be used in conjunction with a second vector encoding one of the following gene products. Alternatively, a single vector encoding both genes may be used. A variety of proteins are encompassed within the invention, some of which are described below.

i. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

ii. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

iii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Immunoprecipitation and Immunoblotting Analysis. Cell lysates were prepared and coimmunoprecipitation of endogenous proteins was performed as described previously (Weber et al., 1999). For coimmunoprecipitation of exogenous proteins, cells were lysed in Ab lysis buffer (20 mM Tris, pH 7.5, 0.5% Triton X-100, 0.5% deoxycholic acid (DOC) and 0.5% SDS, 1 mM EDTA) and immunoprecipitates were subjected immunoblot analysis using anti-c-Mycfl (06-340, Upstate) or anti-ARF (Ab80, GeneTex; 07-543, Upstate) and enhanced chemiluminescence for detection.

Immunofluorescence microscopy. The indicated cells were grown on glass coverslips, fixed and permeablized as described previously (Weber et al., 1999). Cells were incubated with anti-nucleolin (C23, MS-3; Santa Cruz), anti-ARF (Ab80) or anti-c-Myc (C-33; Santa Cruz) at a dilution of 1 µg/ml, and then incubated with the appropriate fluorescence-labeled secondary antibodies, AlexaFluor488 goat anti-mouse IgG or AlexaFluor594 donkey anti-rabbit IgG (Molecular Probes), at a dilution of 1:1000. Fluorescence microscopy was performed as described previously (Weber et al., 1999) using a 63× objective.

Reporter assays. For luciferase assays, ARF$^{-/-}$ MEFs or p53$^{-/-}$ MEFs were seeded at 1×10$^5$ cells per 35 mm dish. The next day, cells were transfected with 1.2 μg of c-Myc and/or 0.3 μg ARF expression vector and 1.2 mg of reporter construct. pRL-TK (500 ng) was included as an internal control. Luciferase assays were carried out according to the manufacturer's instructions (Dual-Luciferase Reporter Assay System; Promega). Results were normalized for expression of pRL-TK as measured by *Renilla* luciferase activity. For SEAP (secreted placental alkaline phosphatase) assays, culture media was collected from cells 36-60 h after transfection, heated at 65° C. for 30 min, and clarified by centrifugation. Culture media was added to 2×SEAP buffer (2M diethanolamine, 1 mM MgCl$_2$, and 20 mM 1-homoarginine) containing 57 mM p-nitrophenyl phosphate (Sigma104 phosphatase substrate) and SEAP activity was measured by spectrophotometry at wavelength 405 nm. Luciferase or SEAP activity from cells transfected with reporter gene alone was standardized to 100%. Normalized values from duplicate samples were reported as the mean±s.d. Each assay is representative of at least three independent studies.

Anchorage-independent growth assay. Rat1a MycER or Rat1a MycER ᵇARF cell lines were plated at 2×10$^4$ cells per 35-mm dish in soft agar containing DMEM plus 10% FCS with 2 μM OHT. Colonies (76 mm or larger) from triplicate plates were counted using an Omnicon colony counter (Bausch & Lomb) on day 10 after plating. Data from the two different monoclonal cells lines shown is representative of at least four different cell lines.

Quantitative real-time PCR. Four mg of total RNA isolated from p53$^{-/-}$MycER MEFs and DKO MycER MEFs treated with 1 μM OHT for the indicated time was reverse-transcribed using the Access RT-PCR system (Promega). Quantitative real-time PCR was performed using the iCycler and SYBR Green dye (BioRad). Relative measurement of gene expression was calculated following manufacturer's instructions using the standard curve method. The specific primer sequences used are listed in Supplementary Information. Relative values compared to the unactivated control samples were graphed as the mean±s.d. from triplicate assays. Each analysis was representative of at least two different monoclonal cell lines.

Chromatin immunoprecipitation (ChIP). p53$^{-/-}$MycER MEFs and DKO MycER MEFs were treated with 5 μM OHT for 4 hr as indicated and the cells were cross-linked with 1% formaldehyde at 37° C. for 10 min. ChIP assays were performed using anti-ARF (Ab80) and the ChIP assay kit (Upstate) according to the manufacturer's instructions. Immunoprecipitated DNA was purified using a QIAquick Spin Kit (Qiagen) and subjected to PCR amplification using specific primer sets for eIF4E and nucleolin.

Plasmids and Expression Vectors. The c-Myc expression vectors pRcCMV-Myc2 and retroviral pWZLneo-Myc2 have been previously described (Gregory et al., 2003; Xiao et al., 1998). To generate Myc-YFP, the EcoR1-BamHI c-Myc fragment was removed from pBabepuro-Myc2ER13 and subcloned into EcoR1-BamH1H-digested pEYFP-N1 (Clontech), resulting in fusion of Yellow Fluorescent Protein (YFP) to the C-terminus c-Myc. To generate pBabepuro-ARF, the EcoR1 fragment digested from pCMV5-ARF (containing mouse p19ARF) was inserted into the EcoR1 site of the retroviral pBabepuro vector. For pBabehygro-Myc2ER, the EcoRI fragment was digested from pBabepuro-Myc2ER was inserted into the EcoRI site of the retroviral pBabehygro vector. All constructs were verified by sequencing. The luciferase and SEAP reporter constructs, htert-SEAP, cul1-luc, gadd45-luc and pdgf br-luc, have been previously described (Greenberg et al., 1999; O'Hagan et al., 2000; Marhin et al., 1997; Oster et al., 2000). pRL-TK was obtained from Promega. c-Myc deletion constructs were made using PCR-mediated mutagenesis (Advantage 2 PCR system; Clontech). All mutations were confirmed by DNA sequencing. To generate c-Myc DN (D 1-167), an ATG in optimal Kozak consensus sequence (ACCATGG) was introduced at amino acid 168 by PCR amplification using the primers

```
                                        (SEQ ID NO:3)
    5' AAGCTTACCATGGGGCACAGCGTCT 3'
    and (SEQ ID NO:4)
    5' GCGTCTAGATAGGTCAGTTTATGCACCAGAG 3'
``` and the cDNA was transferred to pGEM-T Easy Vector (Promega) followed by subcloning into pcDNA3 (Invitrogen). To generate c-Myc DC (D368-439), a TAA stop codon with XbaI site was introduced at amino acid 368 by PCR amplification using the primers

```
5' CTACCAGGCTGCGCGCAAAGAC 3'         (SEQ ID NO:5)
and

5' CGTCTAGACTATTACCTCCTCTGACGTTCC 3' (SEQ ID NO:6)
``` and the PCR product was transferred to pGEM-T Easy Vector followed by SacII/XbaI digestion. The SacIIXbaI c-Myc fragment from pRcCMV-Myc2 was then substituted by the SacIIXbaI c-Myc DC fragment. To generate c-Myc DN+DC (D167+D368-439), the HindIII-BfaI fragment of c-Myc DC was substituted by the HindIII-BfaI fragment of c-Myc DN. To generate c-Myc 1-144, an ATG start codon in Kozak consensus sequence with EcoRI site was introduced at the N-terminus and a TAA stop codon with EcoRI site was introduced at amino acid 145 using the primers

```
5' GAATTCGCCACCACGATGCCCCTC 3'        (SEQ ID NO:7)
and

5' CTAGTGATTTTACAGCTTGGCAGCGGC 3'.    (SEQ ID NO:8)
```

The PCR product was then subcloned into the EcoR1 site of pCMV-Tag2 (Stratagene). For generation of c-Myc 250-367, the same strategy was employed using the primers

```
                                        (SEQ ID NO:9)
    5' GAATTCGCCACCATGGACTCTGAAGAACAA 3'
    and (SEQ ID NO:10)
    5' GGCCTCGAGCTATTAGTTCCTCCTCTGACG 3'.
```

Cell Culture, Transfection, Retroviral Infection. Cos-7 cells, p53−/− MEFs, ARF−/− MEFs, p53/ARF double null (DKO) MEFs and REF112 cells were cultured in DMEM with 10% calf serum. Wild-type MEFs from day 14 embryos were isolated and maintained on a 3T9 protocol and propagated in DMEM with 10% fetal calf serum (FCS). HO16 (c-myc−/−) cells were maintained as previously described (Xiao et al., 1998). Cos-7 cells were transfected using the calcium phosphate method, and MEF cells using Fugene 6 (Roche), with the indicated plasmids. Cells were subjected to analysis approximately 48 hr after transfection. The p53−/− MycER MEFs and DKO MycER MEFs were generated using the retroviral expression vector pBabehygro-Myc2ER as described previously (Xiao et al., 1998). Rat1a stably expressing c-MycER with or without ARF were generated as described previously (Xiao et al., 1998 using the retroviral expression vectors pBabepuro-ARF and pWZLneo-c-Myc2ER.

PCR Primers—Quantitative Real-Time PCR:

```
Nucleolin
fwd: 5' ACACCAGCCAAAGTCATTCC 3'     SEQ ID NO:11
rev: 5' ATCCTCATCACTGTCTTCCTTC 3'   SEQ ID NO:12

CDK4
fwd: 5' GCAGTCTACATACGCAACAC 3'     SEQ ID NO:13
rev: 5' TCGTCTTCTGGAGGCAATC 3'      SEQ ID NO:14 eIF4E
fwd: 5' GGACGGGATTGAGCCTATGTG 3'    SEQ ID NO:15
rev: 5' CAGCAGTGTCTCTAGCCAGAAG 3'   SEQ ID NO:16

Htert
fwd: 5' ATGGCGTTCCTGAGTATGG 3'      SEQ ID NO:17
rev: 5' TGAGTGTCCAGCAGCAAG 3'       SEQ ID NO:18

Cul1
fwd: 5' GCTTGTGGTCGCTTCATAAAC 3'    SEQ ID NO:19
rev: 5' TGTCTTCTAGTTCTGCCTCTTC 3'   SEQ ID NO:20 gadd45
fwd: 5' GCTGGCTGCTGACGAAGAC 3'      SEQ ID NO:21
rev: 5' CGGATGAGGGTGAAATGGAT 3'     SEQ ID NO:22 p15INK4b
fwd: 5' GGTTCCCTCCGCCTTCTG 3'       SEQ ID NO:23
rev: 5' GCCCTCTTCGTGCTTGCA 3'       SEQ ID NO:24
```

ChIP Primers:

```
eIF4E
fwd: 5' AGAGGCCTAAATCCAACTCGGCA 3'  SEQ ID NO:25
rev: 5' AAGGCAATACTCACCGGTTCCACA 3' SEQ ID NO:26

Nucleolin
fwd: 5' GGCGATCTGCTGTCTCTG 3'       SEQ ID NO:27
rev: 5' CAACTGCTTCCCACTTCTC 3'      SEQ ID NO:28
```

Northern Blot Analysis. Total RNA was prepared from cells with TRIzol reagent (Invitrogen). Ten μg of total RNA was separated on 1% agarose, 5.4% formaldehyde denaturing gels and transferred to Hybond-N+ membranes (Amersham). Blots were then UV crosslinked, prehybridized, hybridized, and washed according to the manufacturer's instructions (ULTRAhyb; Ambion). cDNA probes were labeled with [$^{32}$P]-dCTP (ICN) using the Primelt II random labeling kit (Stratagene).

Cell Proliferation and Apoptosis Assays. One day after seeding at $5\times10^4$/35 mm dish in media containing 10% FCS, p53−/− MycER and DKO MycER MEFs were treated with 1 mM OHT as indicated and refed with media containing 1 mM OHT daily. The number of attached cells (living cells) and floating cells (apoptotic cells) was determined in triplicate at the indicated times. Apoptosis was confirmed by detection of caspase-3 activation using a specific antibody (Pab CM1; BD PharMingen). Each time course was representative of at least two different monoclonal cell lines. For growth rate analysis of Rat1a MycER or Rat1a MycER+ARF monoclonal cell lines, cells were seeded and treated as described above except cells were shifted into media containing 20% FCS and 0.25 mM OHT. For the apoptosis assay, Rat1a MycER cell or Rat1a MycER+ARF cell lines were plated at $2.5\times10^5$/35 mm dish and shifted 48 hr later into media containing 0.5% serum without or with 1 mM OHT for 4 days. The number of floating (apoptotic) and attached (living) cells was determined in triplicate at the indicated times. Apoptosis was confirmed using DNA fragmentation analysis as described previously (Xiao et al., 1998. The data was converted to ratio of apoptotic cells to living cells and plotted over time. Representative data is shown from experiments using four different monoclonal cell lines.

Example 2

Results

When ARF was examined as a nucleolar marker during studies examining c-Myc localization in immortalized mouse embryo fibroblasts (MEF) lacking p53, the inventors observed that ARF shifted localization in response to increased c-Myc. In untransfected cells, endogenous ARF protein was found in nucleoli and colocalized with nucleolin (FIGS. 1A-C), as has previously been shown (Weber et al., 1999). In contrast, in cells expressing increased levels of c-Myc-YFP (yellow fluorescent protein), ARF colocalized with c-Myc-YFP in a diffuse nucleoplasmic staining pattern (FIGS. 1D-F). Higher expression of c-Myc resulted in a more complete exclusion of ARF from nucleoli (FIG. 1E, lower cell). Transfection of untagged c-Myc demonstrated that the localization shift is not a result of the fluorescent tag (FIGS. 1G-I). In addition, the shift of endogenous ARF also occurred in wild-type MEF cells (FIGS. 1J-L), suggesting that the p53 status of the cells has no effect on ARF relocalization caused by c-Myc. Together, these results suggest that c-Myc interacts with ARF in the nucleoplasm and prevents its nucleolar localization. However, in other cell lines the inventors have also observed colocalization of ARF and c-Myc in nucleoli on ectopic expression of ARF (M.A.G. and S.R.H., unpublished observations). Datta et al. have also observed colocalization of c-Myc and ARF in nucleoli (Datta et al., 2004). The mechanism and role for this differential localization of c-Myc and ARF are under investigation.

Figure 2:
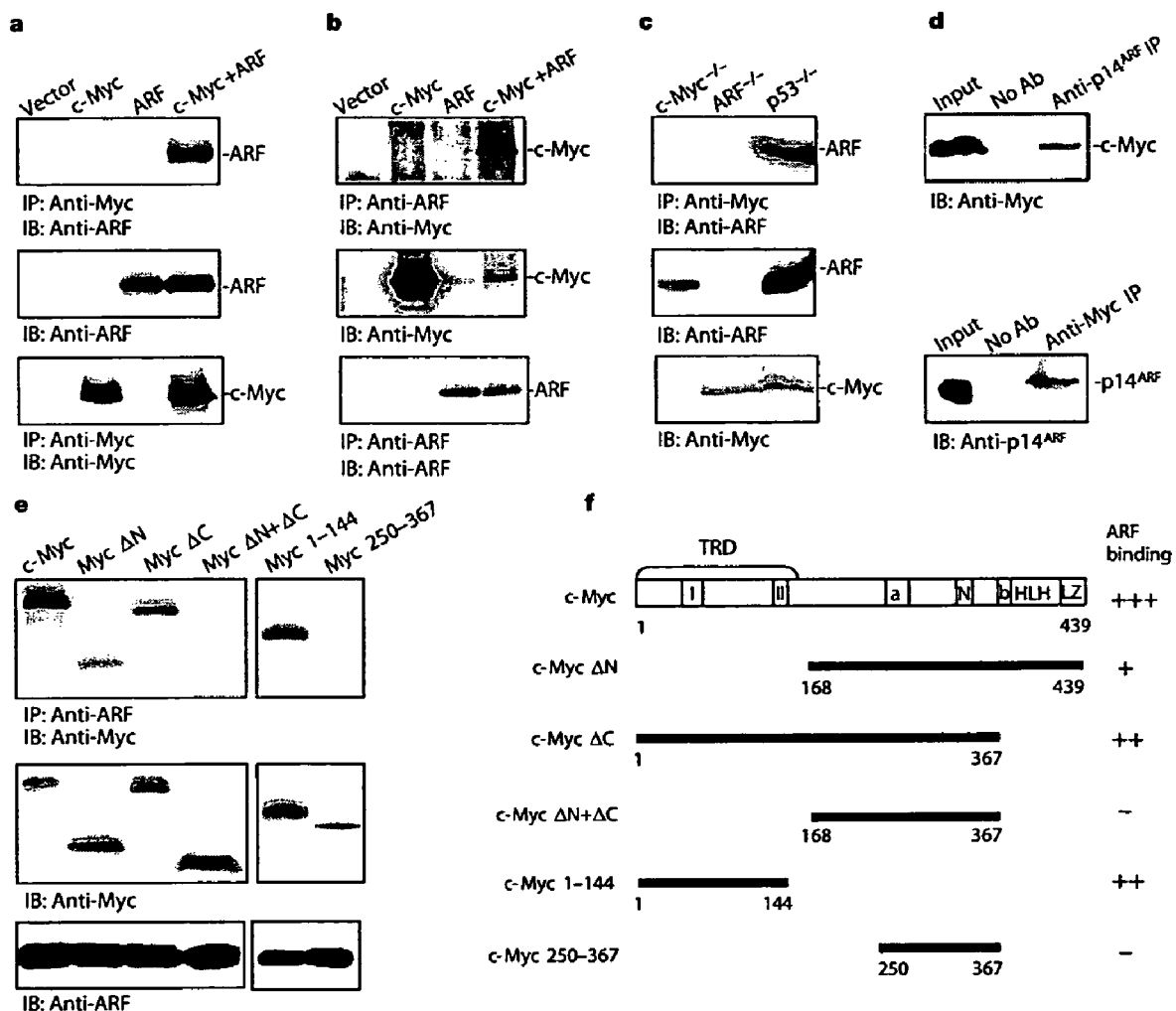
FIGS. 2A-F ARF—binds to c-Myc.

To determine whether the two proteins interact, the inventors expressed c-Myc and ARF individually or together and immunoprecipitation was performed using c-Myc antibody under stringent detergent conditions. Immunoblot analysis was then performed using ARF antibody. When coexpressed, ARF coimmunoprecipitated with c-Myc (FIG. 2A). In the converse experiment, using ARF antibody for immunoprecipitation, c-Myc coprecipitated when coexpressed with ARF (FIG. 2B). Using ARF$^{−/−}$ and c-myc$^{−/−}$ cells as negative controls, we also demonstrated that endogenous ARF coimmunoprecipitates with endogenous c-Myc in p53$^{−/−}$ MEFs (FIG. 2C). Endogenous human p14ARF also specifically coimmunoprecipitated with endogenous human c-Myc from HeLa cells (FIG. 2D).

To identify the domains of c-Myc that interact with ARF, coimmunoprecipitation assays were carried out with a panel of c-Myc proteins having deletions, including deletions of the C-terminal helix-loop-helix/leucine zipper (HLH/LZ) domain, which is necessary for heterodimerization with c-Myc's partner Max, and the amino-terminal transcriptional regulatory domain (TRD), which is critical for transcriptional activation and repression (Grandori and Eisenman, 1997). The c-Myc proteins with deletions of the TRD (DN) or the HLH/LZ (DC) domains were still able to bind ARF, albeit less efficiently (FIG. 2E, left panel), as did all other c-Myc proteins containing different deletions throughout the protein (data not shown). However, deletion of both the TRD and HLH/LZ (DN bDC) resulted in no detectable binding (FIG. 2E, left panel). In addition, an N-terminal fragment (amino acids 1-144) representing the TRD bound efficiently to ARF; whereas an internal fragment (amino acids 250-367) containing the acidic domain showed no detectable binding (FIG. 2E, right panel). Because deletion of the TRD had a greater impact on ARF binding (FIG. 2F), the TRD may represent the primary binding site. These experiments demonstrate that both exogenous and endogenous c-Myc and ARF associate in a highly stable complex and that ARF binds to both the TRD and HLH/LZ domains of c-Myc.

Figure 3:
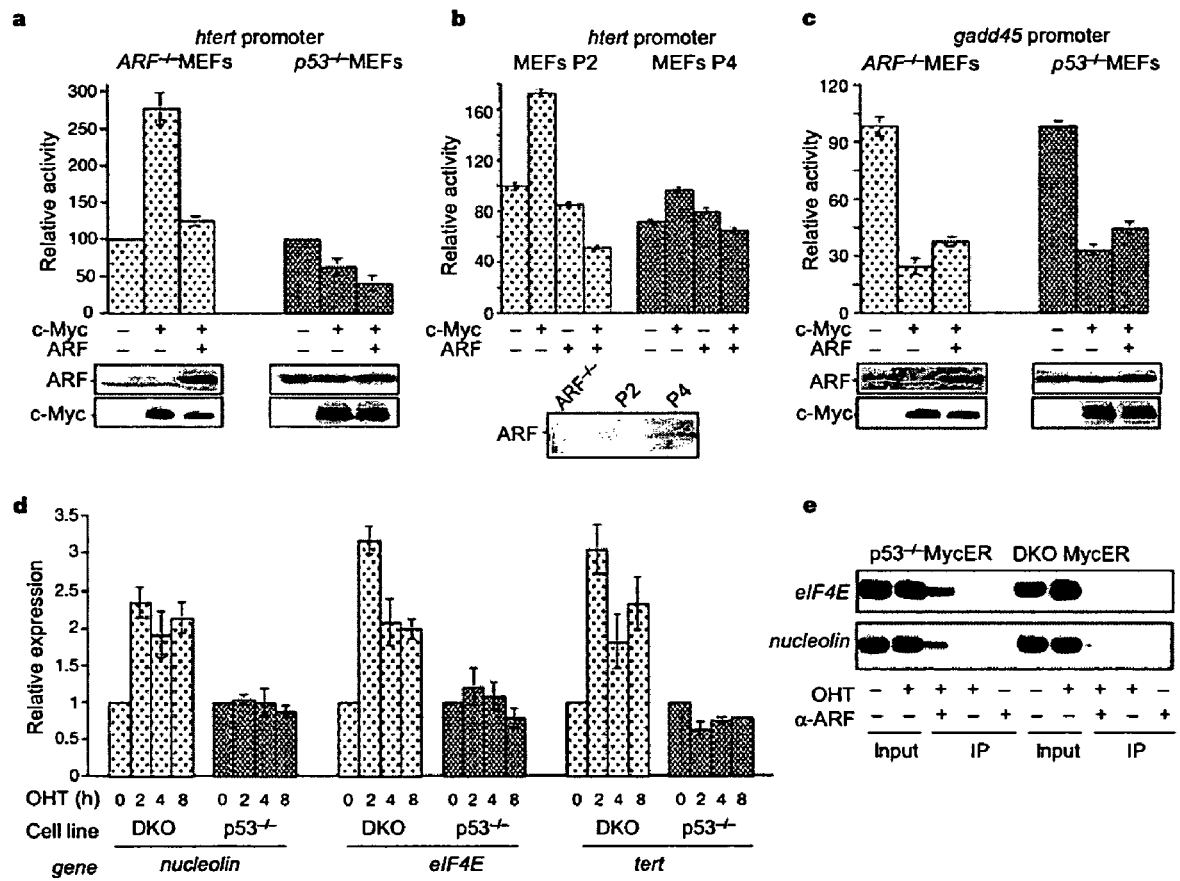
FIGS. 3A-E—ARF differentially regulates the transcriptional activities of c-Myc. Reporter constructs for htert (FIGS. 3A and 3C) and gadd45 (FIG. 3B) promoters were transfected into $\text{ARF}^{-/-}$ MEFs, $p53^{-/-}$ MEFs or embryonic MEFs at the indicated passage number (FIG. 3B), with or without c-Myc or ARF, and reporter activity was determined.
Figure 5:
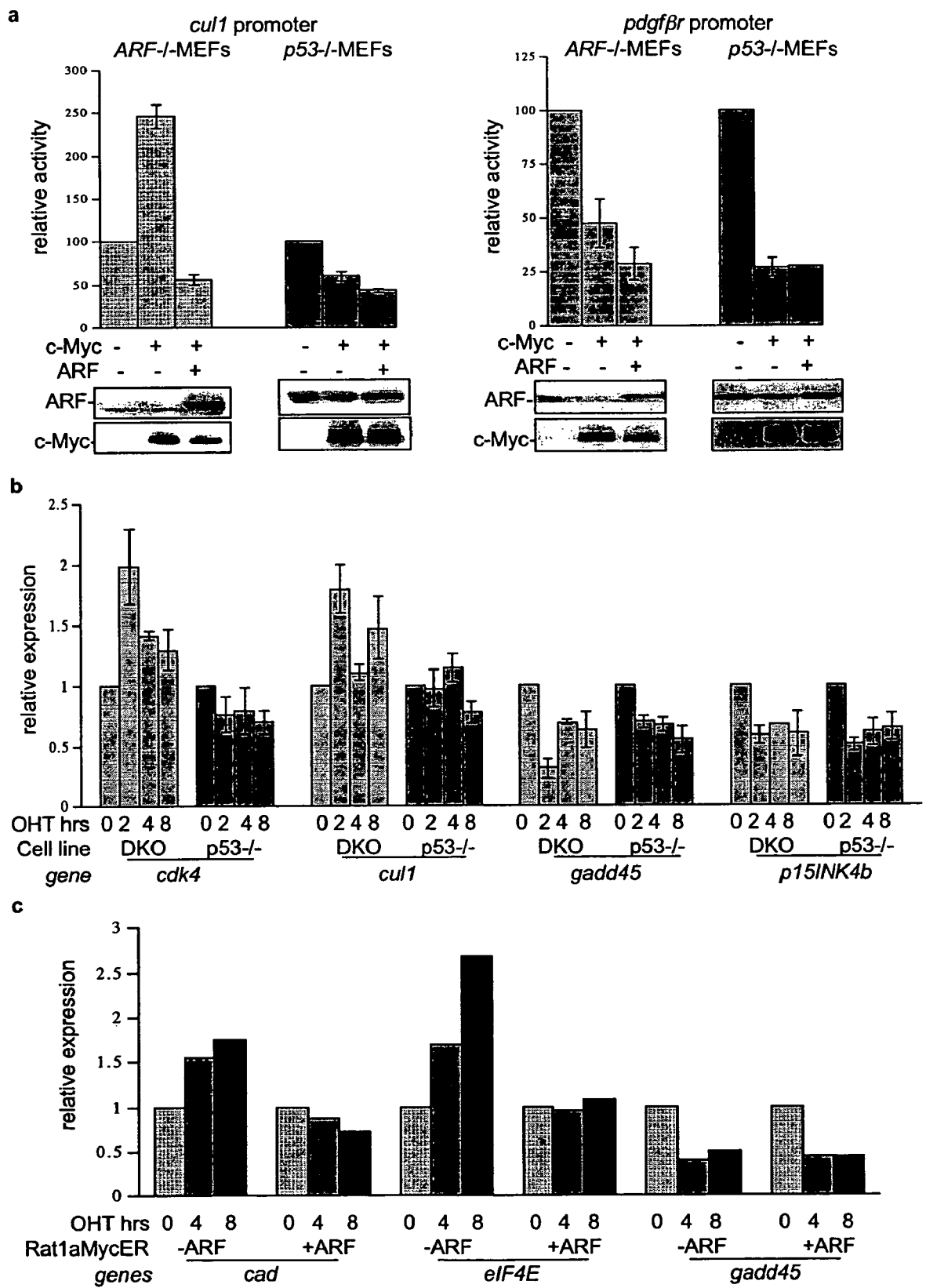
FIGS. 5A-C—ARF differentially regulates the transcriptional activities of c-Myc and blocks the induction of endogenous c-Myc target genes.

ARF binds to regions of c-Myc that are critical for its transcriptional activity, so the inventors next examined the effect of ARF on the activity of c-Myc responsive promoters. In MEF cells lacking ARF (ARF$^{-/-}$), c-Myc alone increased the activation of the telomerase reverse transcriptase (htert) promoter by approximately three-fold (FIG. 3A), which is consistent with earlier reports (Greenberg et al., 1999; Wu et al., 1999). Coexpression of ARF completely blocked the ability of c-Myc to transactivate (FIG. 3A). When c-Myc was expressed in MEF cells having elevated endogenous ARF (p53$^{-/-}$), c-Myc also failed to activate the htert promoter (FIG. 3A). Coexpression of exogenous ARF in these cells resulted in further inhibition of htert promoter activity (FIG. 3A). ARF also blocked the ability of c-Myc to transactivate another c-Myc-responsive promoter, cul1 (O'Hagan et al., 2000) (FIG. 5A), confirming that this effect of ARF is not promoter-specific. In addition, as endogenous ARF levels increase during passaging of primary MEFs4, there is a concordant decrease in c-Myc transactivation. c-Myc transactivated the htert promoter in early passage MEF cells (P2); however, in later passage MEF cells (P4) with higher levels of ARF protein, c-Myc was unable to activate (FIG. 3B). In contrast, there was no effect of exogenous or endogenous ARF on repression of the gadd45 (Marhin et al., 1997) promoter by c-Myc (FIG. 3C). The inventors obtained the same results using another c-Myc-responsive promoter, pdgfbr (Oster et al., 2000) (FIG. 5A). These results suggest that ARF effectively blocks the transactivation function of c-Myc, but not c-Myc's ability to repress transcription.

The inventors next wanted to determine the effect of ARF on the regulation of endogenous c-Myc target genes in a defined p53 null background. Thus, they compared p53/ARF double-knockout (DKO) and p53$^{-/-}$ MEFs that express the chimaeric c-MycER protein (ER, oestrogen receptor), whose activity is inducible upon hydroxytamoxifen (OHT) treatment. Immunofluorescence analysis demonstrated that ARF relocalizes to the nucleoplasm upon activation of c-MycER (data not shown), as shown for transiently expressed c-Myc (FIGS. 1A-L). Real-time polymerase chain reaction (PCR) analyses revealed that activated c-MycER induced the expression of nucleolin, eIF4E, tert, cdk4 and cul1 (FIG. 3D and FIG. 5B) in DKO cells, but there was no upregulation of these genes in p532/2 MEF cells, which have high levels of endogenous ARF. In contrast, the downregulation of gadd45 and p15INK4b by activated c-MycER was not significantly different in DKO compared to p53$^{-/-}$ MEFs (FIG. 5B). In addition, northern blot analyses of Rat1a cells demonstrated that exogenous ARF also blocks upregulation of c-Myc target genes, eIF4E and cad, by activated c-MycER, but does not affect repression of the gadd45 gene (FIG. 5C).

Figure 6:
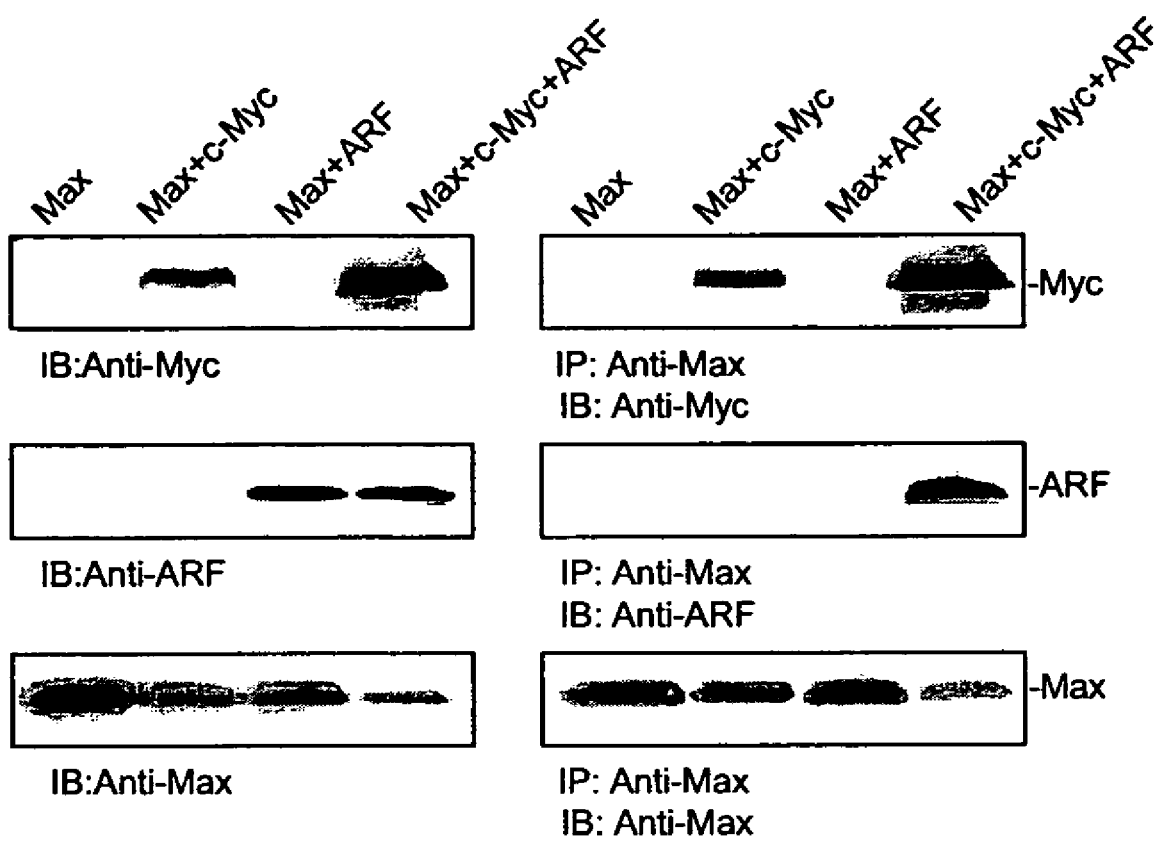
FIG. 6—Coimmunoprecipitation of ARF with c-Myc and Max. Cos-7 cells were transfected with Max alone or together with c-Myc and/or ARF as indicated. Immunoprecipitation (IP) was performed with anti-Max using low stringency buffer (10 mM Tris, pH 7.4, 150 mM NaCl, 0.4% NP-40 and 2 mM EDTA), followed by immunoblot (IB) analysis with anti-Mycfl (upper panel), anti-ARF (middle panel) or anti-Max (lower panel). The lysates were also subjected to direct IB analysis using anti-Mycfl, anti-ARF or anti-Max.

ARF effectively blocked the induction of c-Myc target genes and colocalizes with c-Myc in the nucleoplasm, so the inventors wanted to determine whether ARF protein associates with c-Myc protein at the promoters of c-Myc target genes. Chromatin immunoprecipitation (ChIP) analysis revealed that ARF protein specifically associates with the promoters of eIF4E and nucleolin upon activation of c-MycER in p53$^{-/-}$ MEFs (FIG. 3E). The inventors found no difference between p53$^{-/-}$ and DKO MEFs in ChIP assays using c-Myc antibody (data not shown), suggesting that the presence of ARF does not influence the recruitment of c-Myc to target promoters. c-Myc only binds to target promoters as a heterodimer with Max, so these results suggest that ARF forms a complex with c-Myc and Max. To confirm this, the inventors performed coimmunoprecipitation experiments with Max antibody and found that ARF coprecipitated with c-Myc and Max (FIG. 6). Taken together, these results illustrate that the interaction of ARF with c-Myc differentially controls c-Myc activities by blocking the induction of c-Myc target genes at the promoter without affecting the repression of c-Myc target genes.

Figure 4:
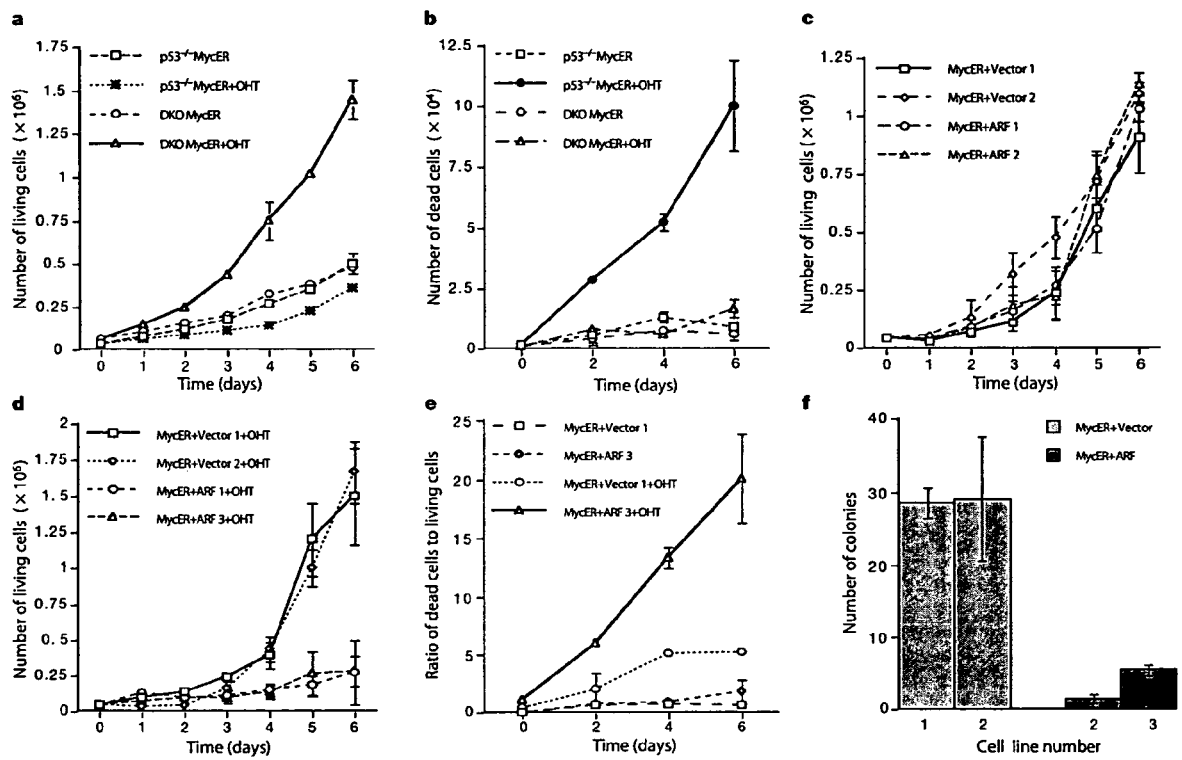
FIGS. 4A-F—ARF inhibits hyperproliferation and transformation by c-Myc, yet facilitates c-Myc-induced apoptosis.

The inventors next wanted to determine whether ARF influences c-Myc biological functions, independently of p53. The inventors examined the proliferation rate of the DKO and p53$^{-/-}$ MEFs expressing c-MycER. Without activation of c-MycER, the p53$^{-/-}$ and DKO MEFs proliferate at similar rates (FIG. 4A). However, upon activation of c-MycER, the p53$^{-/-}$ MEFs accumulated at a slower rate than the control cells, whereas the DKO cells proliferated at a much higher rate (FIG. 4A). There was also a significant increase in the number of apoptotic cells over time upon activation of c-MycER in p53$^{-/-}$ cells, whereas there was no accumulation of apoptotic cells in the DKO or control MEFs (FIG. 4B). These results suggest that ARF inhibits c-Myc-induced hyperproliferation of MEF cells, while enhancing c-Myc-induced apoptosis, independently of p53.

The effects of ARF on c-Myc functions were also examined in Rat1a cells that have been used by the inventors (Xiao et al., 1998) and others (Evan et al., 1992) to demonstrate that c-Myc causes hyperproliferation, transformation and apoptosis in low serum. These cells express low levels of endogenous ARF (FIG. 7A), but do not induce the expression of p53 or p21CIP1 proteins in response to c-MycER activation or ARF overexpression (FIG. 7C). Although the oncogenic pathway of p53 activation appears to be disabled in Rat1a cells, DNA damage from doxorubicin treatment induces low levels of p53 and p21CIP1 (FIG. 7C). These results are in agreement with previous reports that found c-Myc-mediated apoptosis in Rat1a cells to be p53-independent (Harrington et al., 1994; Lenahan and Ozer, 1996). Overexpression of ARF had no effect on Rat1a cellular proliferation in the absence of c-MycER activation (FIG. 7C). However, ARF coexpression effectively blocked activated c-MycER-induced hyperproliferation (FIG. 7D). When the Rat1a cells were shifted to media containing low serum at the time c-Myc was activated, the number of apoptotic cells relative to living cells increased dramatically over time (FIG. 4E). As with the MEF cells, these results probably reflect the combined effects of ARF enhancing c-Myc-induced apoptosis while inhibiting c-Myc induced proliferation of the remaining living cells. Without c-Myc activation, ARF overexpression had no effect on apoptosis (FIG. 4E). In addition, coexpression of ARF sharply reduced the ability of activated c-MycER to induce transformation, as measured by anchorage-independent growth in soft agar (FIG. 4F). These results further confirm that ARF differentially controls c-Myc biological activities, independently of p53.

Although p53 has been proposed to mediate c-Myc-induced apoptosis and ARF-induced apoptosis and growth arrest (Zindy et al., 1998), there are numerous reports demonstrating p53-independent apoptosis in vivo and in vitro caused by c-Myc or ARF (Harrington et al., 1994; Lenahan and Ozer, 1996; Amanullah et al., 2000; Fukasawa et al., 1997; Korgaonkar et al., 2002; Sakamuro et al., 1995; Trudel et al., 1997; Tsuji et al., 2002; Weber et al., 2000). The results suggest that when ARF is induced by elevated c-Myc, it prevents hyperproliferation and transformation through a direct negative-feedback mechanism. Therefore, the loss of ARF could contribute to c-Myc induced tumorigenesis by at least two mechanisms. Consistent with this idea, the down-regulation of ARF/Ink4a by Bmi-1 is probably responsible for the strong collaboration of the bmi-1 and c-myc oncogenes to induce murine lymphomagenesis (Jacobs et al., 1999). In addition, Em-myc-induced lymphomagenesis is greatly accelerated by ARF loss (Eischen et al., 1999), and inactivation of ARF was consistently found in murine myeloid tumours arising from deregulated c-Myc (Haviernik et al., 2003).

These results suggest that ARF blocks c-Myc-induced hyperproliferation and transformation by blocking transactivation of key c-Myc target genes. In contrast, the inability of ARF to block c-Myc-induced apoptosis suggests that c-Myc-induced apoptosis is mediated through another mechanism, perhaps transrepression of specific anti-apoptotic genes. Previous reports also suggest that the mechanism for c-Myc-induced apoptosis is distinct from the mechanism of c-Myc-stimulated proliferation, and that this mechanism is dependent on c-Myc transrepression (Xiao et al., 1998; Evan et al., 1992; Oster et al., 2003; Conzen et al., 2000; Soucek et al., 2002). Therefore, in addition to ARF mediating p53 activation, ARF binding to c-Myc represents an important fail-safe mechanism for preventing aberrant c-Myc signalling and tumorigenesis through differential control of c-Myc transcriptional activities.

ARF is normally localized to the nucleolus. Upon c-Myc overexpression, the inventors found that ARF is relocalized to the nucleoplasm where it colocalizes with c-Myc. These results suggest that c-Myc interacts with endogenous ARF in the nucleoplasm and prevents its nucleolar translocation. However, ARF can also influence c-Myc localization when ARF is exogenously expressed in some types of cells. As shown in FIGS. 8A-C, high overexpression of ARF-CFP in Cos cells results in localization of c-Myc-YFP to nucleoli. As an initial experiment to identify the region of ARF that interacts with c-Myc, we examined a peptide of ARF containing a region that has been previously shown to mediate nucleolar localization. To determine whether this ARF peptide could alter the localization of c-Myc by direct binding, the inventors performed fluorescence microscopy on Cos cells transiently expressing a chimeric protein of the ARF sequence (amino acids 26-44) and GFP. As shown in FIGS. 6D-E, expression of GFP-ARF 26-44 caused c-Myc to localize to the nucleoli as efficiently as full length ARF protein. The inventors have also confirmed by co-immunoprecipitation experiments that this GFP-ARF 26-44 interacts with c-Myc (data not shown). The inventors' recent finding that a small 19-amino acid ARF fragment can bind and colocalize with c-Myc suggests that ARF peptides will also be able to inhibit the transforming activity of c-Myc while enhancing c-Myc-mediated apoptosis.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference.

U.S. Pat. No. 5,466,468
U.S. Pat. No. 5,846,225
U.S. Pat. No. 5,846,233
Amanullah et al., *Oncogene*, 19:2967-2977, 2000.
Arap et al., *Cancer Res.*, 55(6):1351-1354, 1995.
Askew et al., *Oncogene*, 6:1915-1922, 1991.
Baichwal and Sugden, In: *Gene Transfer*, Kucherlapati (Ed.), NY, Plenum Press, 117-148, 1986.
Bakhshi et al., *Cell*, 41(3):899-906, 1985.
Bates et al., *Nature*, 395:124-125, 1998.
Benvenisty and Neshif, *Proc. Natl. Acad. Sci. USA*, 83(24):9551-9555, 1986.
Berg et al., *Proc. Natl. Acad. Sci. USA*, 99:3830-3835, 2002.
Bissonnette et al., *J. Exp. Med.*, 180: 2413-2418, 1994.
Caldas et al., *Nat. Genet.*, 8(1):27-32, 1994.
Capaldi et al., *Biochem. Biophys. Res. Comm.*, 74(2):425-433, 1977.
Carter and Flotte, *Curr. Top Microbiol. Immunol.*, 218:119-144, 1996.
Chatterjee et al., *Ann. NY Acad. Sci.*, 770:79-90, 1995.
Chen and Okayama, *Mol. Cell Biol.*, 7(8):2745-2752, 1987.
Cheng et al., *Cancer Res.*, 54(21):5547-5551, 1994.
Chiu et al., *Electrophoresis*, 23(3):449-455, 2002.
Cleary and Sklar, *Proc. Natl. Acad. Sci. USA*, (21):7439-7443, 1985.
Cleary et al., *J. Exp. Med.*, 164(1):315-320, 1986.
Coffin, In: *Virology*, Fields et al. (Eds.), Raven Press, NY, 1437-1500, 1990.
Conzen et al., *Mol. Cell Biol.*, 20:6008-6018, 2000.
Coupar et al., *Gene*, 68:1-10, 1988.
Culver et al., *Science*, 256(5063):1550-1552, 1992.
Datta et al., *J. Biol. Chem.*, 279:36698-36707, 2004.
Dubensky et al., *Proc. Natl. Acad. Sci. USA*, 81:7529-7533, 1984.
Eischen et al., *Genes Dev.*, 13:2658-2669, 1999.
EPO 0 273 085
Evan et al., *Cell*, 69:119-128, 1992.
Facchini and Penn, *FASEB J.*, 12:633-651, 1998.
Fechheimer et al., *Proc. Natl. Acad. Sci. USA*, 84:8463-8467, 1987.
Felsher and Bishop, *Mol. Cell*, 4:199-207, 1999.
Felsher and Bishop, *Proc. Natl. Acad. Sci. USA*, 96:3940-3944, 1999.
Ferkol et al., *FASEB J*, 7:1081-1091, 1993.
Ferrari et al., *J. Virol.*, 70(5):3227-3234, 1996.
Fisher et al., *Hum. Gene Ther.*, 7(17):2079-2087, 1996.
Flotte and Carter, *Gene Ther.*, 2(6):357-62, 1995.
Flotte et al., *Proc. Natl. Acad. Sci. USA*, 90(22):10613-10617, 1993.

Forster, *Ann. Phys.*, 2:55-75, 1948.
Fraley et al., *Proc. Natl. Acad. Sci. USA*, 76:3348-3352, 1979.
Fukasawa et al., *Oncogene*, 15:1295-1302, 1997.
Gasmi et al., *J. Virol.*, 73(3):1828-1834, 1999.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Goodman et al., *Blood*, 84(5):1492-1500, 1994.
Gopal, *Mol. Cell Biol.*, 5:1188-1190, 1985.
Gorczyca et al., *Cancer Res.*, 53(8):1945-1951, 1993.
Graham and Van Der Eb, *Virology*, 52:456-467, 1973.
Grandori and Eisenman, *Trends Biochem.*, 22:177-181, 1997.
Greenberg et al., *Oncogene*, 18(5):1219-1226, 1999.
Gregory et al., *J. Biol. Chem.*, 278:51606-51612, 2003.
Harland and Weintraub, *J. Cell Biol.*, 101(3):1094-1099, 1984.
Harrington et al., *EMBO J.*, 13:3286:3295, 1994.
Haviernik et al., *Oncogene*, 22:1600-1610, 2003.
Hay et al., *J. Molec. Biology*, 175:493-510, 1984.
Hearing and Shenk, *J. Molec. Biology*, 167:809-822, 1983.
Hearing et al., *J. Virology*, 67:2555-2558, 1987.
Henriksson and Luscher, *Adv. Cancer Res.*, 68:109-182, 1996.
Hollstein et al., *Science*, 253(5015):49-53, 1991.
Honda and Yasuda, *EMBO J.*, 18(1):22-27, 1999.
Hussussian et al., *Nat. Genet.*, 8(1):15-21, 1994.
Jacobs et al., *Genes Dev.*, 13:2678-2690, 1999.
Jain et al., *Science*, 297:102-104, 2002.
Kamb et al., *Nat. Genet.*, 8(1):23-26, 1994a.
Kamb et al., *Science*, 2674:436-440, 1994b.
Kamijo et al., *Cancer Res.*, 59:2217-2222, 1999.
Kaneda et al., *Science*, 243:375-378, 1989.
Kaplitt et al., *Ann. Thorac. Surg.*, 62(6):1669-1676, 1996.
Kaplitt et al., *Nat Genet.*, 8(2):148-54, 1994.
Kato et al, *J. Biol. Chem.*, 266:3361-3364, 1991.
Kerr et al., *Br. J. Cancer*, 26(4):239-257, 1972.
Kessler et al., *Proc. Natl. Acad. Sci. USA*, 93(24):14082-14087, 1996.
Klein et al., *Nature*, 327:70-73, 1987.
Koeberl et al., *Proc. Natl. Acad. Sci. USA*, 94(4):1426-1431, 1997.
Korgaonkar et al., *Mol. Cell Biol.*, 22:196-206, 2002.
Lemaitre et al., *Adv. Cancer Res.*, 70:95-144, 1996.
Lenahan and Ozer, *Oncogene*, 12:1847-1854, 1996.
Levrero et al., *Gene*, 101: 195-202, 1991.
Li and Dang, *Mol. Cell Biol.*, 19:5339-5351, 1999.
Lohrum et al., *Curr. Biol.*, 10(9):539-542, 2000.
Mann et al., *Cell*, 33:153-159, 1983.
Marhin et al., *Oncogene*, 14:2825-2834, 1997.
McCown et al., *Brain Res*, 713(1-2):99-107, 1996.
Midgley et al., *Oncogene*, 19(19):2312-2323, 2000.
Mizukami et al., *Virology*, 217(1):124-130, 1996.
Mori et al., *Cancer Res.*, 54(13):3396-3397, 1994.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nobri et al., *Nature (London)*, 368:753-756, 1995.
O'Hagan et al., *Genes Dev.*, 14:2185-2191, 2000.
Okamoto et al., *Proc. Natl. Acad. Sci. USA*, 91(23):11045-11049, 1994.
Orlow et al., *Cancer Res.*, 54(11):2848-2851, 1994.
Orlow et al., *Int. J. Oncol.*, 15(1):17-24, 1994.
Oster et al., *Adv. Cancer Res.*, 84:81-154, 2002.
Oster et al., *Mol. Cell Biol.*, 20:6768-6778, 2000.
Oster et al., *Oncogene*, 22:1998-2010, 2003.
Paskind et al., *Virology*, 67:242-248, 1975.
Patterson et al., *Anal. Biochem.*, 284(2):438-440, 2000.
PCT Appln. WO 84/03564
Perales et al., *Proc. Natl. Acad. Sci. USA*, 91:4086-4090, 1994.
Phizicky and Fields, *Microbiol. Rev.*, 59(1):94-123, 1995.
Ping et al., *Microcirculation*, 3(2):225-228, 1996.
Pomerantz et al., *Cell*, 92:713-723, 1998.
Potter et al., *Proc. Natl. Acad. Sci. USA*, 81:7161-7165, 1984.
Radler et al., *Science*, 275:810-814, 1997.
Remington's Pharmaceutical Sciences, 15$^{th}$ Ed., 1035-1038; 1570-1580, Mack Publishing Company, Easton, Pa., 1980.
Renan, *Radiother. Oncol.*, 19:197-218, 1990.
Ridgeway, In: *Vectors: A survey of molecular cloning vectors and their uses*, Rodriguez and Denhardt (Eds.), Stoneham: Butterworth, 467-492, 1988.
Rippe et al., *Mol. Cell Biol.*, 10:689-695, 1990.
Roux et al., *Proc. Natl. Acad. Sci. USA*, 86:9079-9083, 1989.
Sakamuro et al., *Oncogene*, 11:2411-2418, 1995.
Sambrook et al., In: *Molecular cloning*, Cold Spring Harbor Laboratory Press, Cold Spring Harbor, N.Y., 2001.
Samulski et al., *J. Virol.*, 61(10):3096-3101, 1987.
Serrano et al., *Nature*, 366:704-707, 1993.
Serrano et al., *Science*, 267(5195):249-252, 1995.
Soucek et al., *Cancer Res.*, 62:3507-3510, 2002.
Spencer and Groudine, *Adv. Cancer Res.*, 56:1-48, 1991.
Temin, In: *Gene Transfer*, Kucherlapati (Ed.), NY, Plenum Press, 149-188, 1986.
Tibbetts, *Cell*, 12:243-249, 1977.
Trudel et al., *J. Exp. Med.*, 186:1873-1884, 1997.
Tsuji et al., *Biochem. Biophys. Res. Commun.*, 295:621-629, 2002.
Tsujimoto and Croce, *Proc. Natl. Acad. Sci. USA*, 83(14): 5214-5218, 1986.
Tsujimoto et al., *Science*, 228(4706):1440-1443, 1985.
Tur-Kaspa et al., *Mol. Cell Biol.*, 6:716-718, 1986.
Wagner et al., *Proc. Natl. Acad. Sci. USA* 87(9):3410-3414, 1990.
Watt et al., *Proc. Natl. Acad. Sci.*, 83(2):3166-3170, 1986.
Weber et al., *Genes Dev.*, 14(18):2358-2365, 2000.
Weinberg, *Science*, 254(5035):1138-1146, 1991.
White et al. *J. Virol.*, 73(4):2832-2840, 1999.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu et al., *Nat. Genet.*, 21:220-224, 1999.
Xiao et al., *Genes Dev.*, 12:3803-3808, 1998.
Xiao et al., *J. Virol.*, 70:8098-8108, 1996.
Yang et al., *Proc. Natl. Acad. Sci. USA*, 87:9568-9572, 1990.
Zhang et al., *Cell*, 92:725-734, 1998.
Zindy et al., *Genes Dev.*, 12:2424-2433, 1998.

What is claimed is:

1. A method of screening a candidate substance comprising:
   (a) providing an isolated c-Myc polypeptide;
   (b) mixing said c-Myc polypeptide with a candidate substance;
   (c) mixing the mixture of step (b) with p19Arf polypeptide; and
   (d) measuring the binding of p19Arf and c-Myc polypeptides,
   wherein a decrease in p19Arf polypeptide binding to c-Myc polypeptide, as compared to the binding of p19Arf polypeptide to c-Myc polypeptide in the absence of said candidate substance, identifies said candidate substance as a p19Arf mimic.

2. The method of claim 1, wherein said p19Arf and c-Myc polypeptides is are murine polypeptides.

3. The method of claim 2, wherein said p19Arf polypeptide has the sequence of SEQ ID NO:1.

4. The method of claim 1, wherein at least one of said p19Arf and c-Myc polypeptides is labeled.

5. The method of claim 4, wherein both of said p19Arf and c-Myc polypeptides are labeled.

6. The method of claim 5, wherein the p19Arf and c-Myc labels permit measurement of fluorescence resonance energy transfer.

7. The method of claim 1, wherein the candidate substance is a peptide, a polypeptide, a oligonucleotide, a polynucleotide, or small molecule.

8. The method of claim 1, wherein step (d) comprises separation by gel electrophoresis.

9. The method of claim 1, wherein step (d) comprises immunologic detection.

10. The method of claim 1, wherein c-Myc polypeptide is bound to a support, and step (d) comprises measuring p19Arf bound to said support.

11. The method of claim 10, wherein said p19Arf polypeptide is labeled, and step (d) comprises measuring label associated with said support.

12. The method of claim 10, wherein the support is a column, a bead, a dipstick, a microtiter well or a test tube.

13. The method of claim 11, wherein c-Myc is labeled, and the p19Arf and c-Myc labels permit measurement of fluorescence resonance energy transfer.

14. The method of claim 10, wherein step (d) comprises contacting said support with an anti-p19Arf antibody that binds p19Arf polypeptide when bound to c-Myc polypeptide.

15. The method of claim 10, further comprising a washing step between steps (b) and (c), between steps (c) and (d), or both.

* * * * *

UNITED STATES PATENT AND TRADEMARK OFFICE
CERTIFICATE OF CORRECTION

PATENT NO. : 7,625,716 B2  Page 1 of 1
APPLICATION NO. : 10/997763
DATED : December 1, 2009
INVENTOR(S) : Stephen R. Hann It is certified that error appears in the above-identified patent and that said Letters Patent is hereby corrected as shown below:

Title Page item (54) title, delete
"METHODS FOR ASSESSING P19-ARF INTERACTIONS IN CMYC"
and insert
--METHODS FOR ASSESSING P19-ARF INTERACTIONS WITH CMYC-- therefor.

In column 1, lines 1-2, delete
"METHODS FOR ASSESSING P19-ARF INTERACTIONS IN CMYC"
and insert
--METHODS FOR ASSESSING P19-ARF INTERACTIONS WITH CMYC-- therefor.

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,625,716 B2 | Page 1 of 1 |
| APPLICATION NO. | : 10/997763 | |
| DATED | : December 1, 2009 | |
| INVENTOR(S) | : Hann | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this

Fifth Day of October, 2010

David J. Kappos
*Director of the United States Patent and Trademark Office*

SEQUENCE LISTING

<160> NUMBER OF SEQ ID NOS: 29

<210> SEQ ID NO 1
<211> LENGTH: 169
<212> TYPE: PRT
<213> ORGANISM: Mus musculus

<400> SEQUENCE: 1

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
            20                  25                  30

Pro Arg Thr Ala Ser Cys Ala Leu Ala Phe Val Asn Met Leu Leu Arg
        35                  40                  45

Leu Glu Arg Ile Leu Arg Arg Gly Pro His Arg Asn Pro Gly Pro Gly
    50                  55                  60

Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Ala
                85                  90                  95

Arg Arg Ser Ala Gly Arg Leu Pro Gly His Ala Gly Gly Ala Ala Arg
            100                 105                 110

Val Arg Gly Ser Ala Gly Cys Ala Arg Cys Leu Gly Ser Pro Ala Ala
        115                 120                 125

Arg Leu Gly Pro Arg Ala Gly Thr Ser Arg His Arg Ala Ile Phe Ala
130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

<210> SEQ ID NO 2
<211> LENGTH: 19
<212> TYPE: PRT
<213> ORGANISM: Mus macedonicus

<400> SEQUENCE: 2

Lys Phe Val Arg Ser Arg Arg Pro Arg Thr Ala Ser Cys Ala Leu Ala
1               5                   10                  15

Phe Val Asn

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
aagcttacca tggggcacag cgtct                                             25

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gcgtctagat aggtcagttt atgcaccaga g                          31

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ctaccaggct gcgcgcaaag ac                                    22

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cgtctagact attacctcct ctgacgttcc                            30

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gaattcgcca ccacgatgcc cctc                                  24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ctagtgattt tacagcttgg cagcggc                               27

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gaattcgcca ccatggactc tgaagaacaa                            30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 10
ggcctcgagc tattagttcc tcctctgacg                                      30

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
acaccagcca aagtcattcc                                                 20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
atcctcatca ctgtcttcct tc                                              22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gcagtctaca tacgcaacac                                                 20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tcgtcttctg gaggcaatc                                                  19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ggacgggatt gagcctatgt g                                               21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
```

```
cagcagtgtc tctagccaga ag                                              22

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
atggcgttcc tgagtatgg                                                  19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
tgagtgtcca gcagcaag                                                   18

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gcttgtggtc gcttcataaa c                                               21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
tgtcttctag ttctgcctct tc                                              22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gctggctgct gacgaagac                                                  19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
```

-continued cggatgaggg tgaaatggat                                            20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ggttccctcc gccttctg                                              18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
gccctcttcg tgcttgca                                              18

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
agaggcctaa atccaactcg gca                                        23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
aaggcaatac tcaccggttc caca                                       24

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ggcgatctgc tgtctctg                                              18

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
caactgcttc ccacttctc                                             19

```
<210> SEQ ID NO 29
<211> LENGTH: 132
<212> TYPE: PRT
<213> ORGANISM: Homo sapiens

<400> SEQUENCE: 29

Met Val Arg Arg Phe Leu Val Thr Leu Arg Ile Arg Arg Ala Cys Gly
 1               5                  10                  15

Pro Pro Arg Val Arg Val Phe Val Val His Ile Pro Arg Leu Thr Gly
             20                  25                  30

Glu Trp Ala Ala Pro Gly Ala Pro Ala Ala Val Ala Leu Val Leu Met
         35                  40                  45

Leu Leu Arg Ser Gln Arg Leu Gly Gln Gln Pro Leu Pro Arg Arg Pro
     50                  55                  60

Gly His Asp Asp Gly Gln Arg Pro Ser Gly Gly Ala Ala Ala Ala Pro
 65                  70                  75                  80

Arg Arg Gly Ala Gln Leu Arg Arg Pro Arg His Ser His Pro Thr Arg
                 85                  90                  95

Ala Arg Arg Cys Pro Gly Gly Leu Pro Gly His Ala Gly Gly Ala Ala
            100                 105                 110

Pro Gly Arg Gly Ala Ala Gly Arg Ala Arg Cys Leu Gly Pro Ser Ala
        115                 120                 125

Arg Gly Pro Gly
    130
```